(12) United States Patent
Rowatt et al.

(10) Patent No.: US 9,382,433 B2
(45) Date of Patent: Jul. 5, 2016

(54) KETOCOUMARINS AS PHOTOINITIATORS AND PHOTOSENSITIZERS IN PRINTING INKS AND COATINGS

(71) Applicant: SUN CHEMICAL CORPORATION, Parsippany, NJ (US)

(72) Inventors: Brian Rowatt, Maidstone (GB); Shaun Herlihy, Walderslade (GB); Robert Davidson, Leicester (GB)

(73) Assignee: SUN CHEMICAL CORPORATION, Parsippany, NJ (US)

( * ) Notice: Subject to any disclaimer, the term of this patent is extended or adjusted under 35 U.S.C. 154(b) by 0 days.

(21) Appl. No.: 14/417,299

(22) PCT Filed: Jul. 26, 2013

(86) PCT No.: PCT/US2013/052184
§ 371 (c)(1),
(2) Date: Jan. 26, 2015

(87) PCT Pub. No.: WO2014/018826
PCT Pub. Date: Jan. 30, 2014

(65) Prior Publication Data
US 2015/0210869 A1    Jul. 30, 2015

Related U.S. Application Data

(60) Provisional application No. 61/676,370, filed on Jul. 27, 2012.

(51) Int. Cl.
| | |
|---|---|
| *A01M 1/20* | (2006.01) |
| *A61L 2/08* | (2006.01) |
| *C08F 2/46* | (2006.01) |
| *C08F 2/50* | (2006.01) |
| *C08G 61/04* | (2006.01) |
| *C09D 11/101* | (2014.01) |
| *C07D 311/16* | (2006.01) |
| *C07D 311/08* | (2006.01) |
| *C09D 11/30* | (2014.01) |
| *C09D 133/14* | (2006.01) |
| *C09D 133/06* | (2006.01) |
| *C09D 4/00* | (2006.01) |

(52) U.S. Cl.
CPC ............ *C09D 11/101* (2013.01); *C07D 311/08* (2013.01); *C07D 311/16* (2013.01); *C09D 11/30* (2013.01); *C09D 133/068* (2013.01); *C09D 133/14* (2013.01); *C09D 4/00* (2013.01); *C09D 133/06* (2013.01)

(58) Field of Classification Search
USPC .......................... 422/36, 28, 1; 522/1; 520/1
See application file for complete search history.

(56) References Cited

U.S. PATENT DOCUMENTS

| | | | |
|---|---|---|---|
| 7,544,721 B2 | 6/2009 | Gaud et al. | |
| 7,875,698 B2 | 1/2011 | Vanmaele et al. | |
| 2012/0142793 A1* | 6/2012 | Frey et al. | 521/50.5 |

FOREIGN PATENT DOCUMENTS

| | | |
|---|---|---|
| CN | 1599735 A | 3/2005 |
| EP | 0022188 B1 | 10/1984 |
| WO | 03/033452 A1 | 4/2003 |

OTHER PUBLICATIONS

Brunet et al, Novel polyamioncarboxylate chelates derived from 3-aroylcoumarins, 2001, Tetrahedron, 57, 3105-3116.*
International Search Report and Written Opinion mailed on Dec. 23, 2013 in connection with International Application No. PCT/US2013/052184.
Chinese Office Action issued in Chinese Application No. 201380039362.5 dated Dec. 9, 2015 (with English Language Translation).
International Preliminary Report from International Application PCT/US2013/052184, dated Jan. 27, 2015.

* cited by examiner

*Primary Examiner* — Ling Choi
*Assistant Examiner* — Jessica E Whiteley
(74) *Attorney, Agent, or Firm* — Charles C. Achkar; Ostrolenk Faber LLP

(57) ABSTRACT

A series of novel ketocoumarin photoinitiators are disclosed for use in radiation curing.

20 Claims, No Drawings

KETOCOUMARINS AS PHOTOINITIATORS AND PHOTOSENSITIZERS IN PRINTING INKS AND COATINGS

CROSS REFERENCE TO RELATED APPLICATIONS

This application is a §371 National Phase application based on PCT/US2013/052184 filed Jul. 26, 2013, which claims the benefit of U.S. Provisional Patent Application No. 61/676,370, filed on Jul. 27, 2012, the disclosure of which is hereby fully incorporated herein by reference.

FIELD OF THE INVENTION

The present invention relates to a series of novel ketocoumarin photoinitiators for use in radiation curing, for example in the radiation curing of coating compositions such as printing inks or varnishes. Typical areas where these materials could be used are offset, flexo, inkjet, gravure, intaglio and screen where the inks/coatings are cured by UV radiation. The novel ketocoumarins of the present invention exhibit good reactivity, improved solubility and good print properties compared to existing materials of this type.

BACKGROUND OF THE INVENTION

There are many papers/patents on the synthesis of ketocoumarins of the following type:

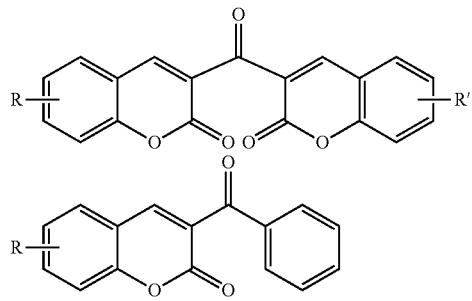

The original process for making ketocoumarins was patented in 1954, by Kurt Knoevenagel (GB752528—30 Sep. 1954). Since then there have been various papers and patents describing the synthesis of ketocoumarins.

Eastman Chemical Co.—Tetrahedron, 38(9), 1203-1211 (1982), and U.S. Pat. No. 4,147,552 (2 Feb. 1976), EP0022188 (18 Jun. 1979)—describe the synthesis of both types shown above with various substituents. Eastman is also claiming their use as spectral sensitizers/co-initiators.

The synthesis of 3-aroylcoumarins has also been patented by Perm. Pharmaceutical Institute USSR as SU707197 USSR (21 Sep. 1978).

More recently there has been some process patents filed on more environmentally friendly production such as solvent free syntheses, e.g. Formulation for Scientific Technology Promotion; JP2002179666 (15 Dec. 2000); Grunenthal GmbH WO2004002980 (1 Jul. 2002).

There have also been many papers and patents on the synthesis of ketocoumarins with various functional groups attached, e.g. 3M have a family of patents with a priority date of 25 Oct. 1991 (U.S. Pat. No. 5,480,994, U.S. Pat. No. 5,455,143, EP0538997, U.S. Pat. No. 5,415,976, and U.S. Pat. No. 5,534,633). These patents claim many functional groups but seem to focus mainly on amine functionality.

Many other companies have also patented di-alkyl amino functional materials and their use as photoinitiator sensitizers, e.g. Thiokol Morton Inc., PH26210 and U.S. Pat. No. 4,894,314 (12 Nov. 1986); Toppan Printing, JP3070704 (10 Aug. 1989); Toyo Ink Mfg., JP5230118 and JP2727851 (19 Feb. 1992), JP4145102 (5 Oct. 1990; Eastman, CA1137696 (16 Nov. 1979); Cookson, JP2000869 (4 Dec. 1987); Tokuyama Corp., US2004186195 and EP1431315 (18 Dec. 2002).

Other synthesis patents include, for example: The sulfonation of ketocoumarins, materials used as photoresists—Clariant Int. Ltd., TW518332 and WO9839318 (7 Mar. 1997); Acrylated ketocoumarin—this material is claimed but no example is given on how to make it. LG Chemical Ltd., KR20090108154 (11 Apr. 2008). LG are claiming this type of material as photosensitive photoinitiators.

Ketocoumarin materials with acrylate functional groups have also been made by Ciba (e.g. WO2005014677). The application of the materials in this patent is as sensitizers for liquid crystals.

Examples of prior art related to certain types of ketocoumarins as photoinitiators include: Acrylated ketocoumarin, LG Chemical Ltd., KR20090108154 (11 Apr. 2008). LG are claiming this type of material as a photosensitive photoinitiator; Eastman Chemical Co.—Tetrahedron, 38(9), 1203-1211 (1982), and U.S. Pat. No. 4,147,552 (2 Feb. 1976), EP0022188 (18 Jun. 1979) and JP1048059 (24 Jul. 1987). Eastman claims the use of ketocoumarins as sensitizers in combination with amine functional materials. A huge range of ketocoumarin structures are claimed with various substituents used; National Super Chim Mulhouse—the use of thioxanthones and ketocoumarins as photoinitiators using visible laser light in the presence of amines and onium salts. Journal of Applied Polymer Science, (1992), 44(10), 11779-86; Bulletin des Societes Chimiques Belges, (1990), 99(11-12), 969-975; Surface Active Photoinitiators. Ciba, WO0248204, WO0248203, WO0248202 (13 Dec. 2000). Organopolysiloxanes have photoinitiator groups attached and are concentrated on the surface of the composition to improve cure. These patents outline the synthesis process of various photoinitiator types and the binding of these materials onto organopolysiloxanes and their cure properties. No cure results are reported for the ketocoumarin type materials; Ketocoumarins attached to polysilsesquioxane materials. Useful as low migration photoinitiators. Amine synergist groups are also incorporated. The patent mainly describes other more common PI types and their cure properties. No cure properties are given for the ketocoumarin type materials. Ciba/BASF WO2010063612 and EP2370449 (1 Dec. 2008); Ketocoumarins attached as pendant groups to a polyalkylene oxide. Oxirane functional photoinitiators have been made and attached via an in-situ reaction with alkylene oxides (the alkylene oxides forming linear polymers). The examples given in the patent are for Benzophenones. No examples of ketocoumarins are given but they are in the claims. Coloplast A/S WO2011103878 (23 Feb. 2010).

There are a number of patents which describe the use of certain ketocoumarins as photosensitizers for photopolymerization processes when used in combination with various other materials, e.g. Titanocenes: Hitachi, TW434455, U.S. Pat. No. 5,811,218 and EP0636939 (28 Jul. 1993), JP7271028 (28 Sep. 1993), JP11209613 and JP11209614 (30 Jan. 1998), JP2000258907 (11 Mar. 1999); Mitsui Toatsu Chemicals, JP9227547 (20 Feb. 1996); Ciba-Geigy Corp., U.S. Pat. No. 5,011,755 (2 Feb. 1997).

Maleimides have been used with many different functional ketocoumarins to improve the polymerization of HDDA, for example: Albemarle Corp., Univ. Of Southern Mississippi, WO2004089995 (3 Apr. 2003).

Borates have been used with functional ketocoumarins, for example Toyo Boseki, JP2157760 (10 Dec. 1988).

Imidazoles/Thiols/Amines have been used with functional ketocoumarins, for example Mitsubishi Chem. Ind., JP61123603 (19 Nov. 1984).

Dual cure with cationic photoinitiators and ferrocene have been used with functional ketocoumarins, for example Nippon-Soda, JP7196712 (28 Dec. 1993).

Active halogen compounds such as trihalofunctional triazines or sulfonylchlorides have been used with functional ketocoumarins, for example Fuji Photo Film Co. Ltd., JP58015503 and U.S. Pat. No. 4,505,793 (20 Jul. 1981).

Ketocoumarins have been used as a sensitizer in combination with organic peroxides, triazines, benzophenones, quinones, N-phenyl glycine and alkyl aryl ketones; and used in liquid injection recording head, for example Canon KK, JP4294148 (25 Mar. 1991); Canon KK/Sanyo Chemical Ind., JP63270703 and JP63145304 (9 Dec. 1986).

Amine functional ketocoumarins have been used as sensitizers with iodonium salts and triazine materials, for example 3M family of patents with a priority date of 25 Oct. 1991 (U.S. Pat. No. 5,480,994, U.S. Pat. No. 5,455,143, EP0538997, U.S. Pat. No. 5,415,976, U.S. Pat. No. 5,534,633. These patents focus mainly on amine functional ketocoumarins as sensitizers.

Aminofunctional ketocoumarins have been used as sensitizers with camphorquinone, dialkylaminobenzoates and imidazolyl dimmers, for example Thiokol Morton Inc., PH26210 and U.S. Pat. No. 4,894,314 (12 Nov. 1986).

Amino functional ketocoumarins have been used as sensitizers with diaryliodonium salts and organic peroxides, for example Toppan Printing, JP3070704 (10 Aug. 1989).

Amino functional ketocoumarins have been used as sensitizers with cationic sulfonium salts, for example Toyo Ink Mfg., JP5230118 and JP2727851 (19 Feb. 1992), JP4145102 (5 Oct. 1990.

Amino functional ketocoumarins have been used as sensitizers with phenyl glycine and indoleacetic acid, for example Eastman, CA1137696 (16 Nov. 1979).

Amino functional ketocoumarins have been used as sensitizers with triazine functional materials, for example Cookson, JP2000869 (4 Dec. 1987).

Amino functional ketocoumarins have been used as sensitizers in a dual cure system with sulfonium salts, Iodonium salts and polycyclic aromatic materials, for example Tokuyama Corp., US2004186195 and EP1431315 (18 Dec. 2002).

Ketocoumarins have been used as sensitizers for aromatic-onium salts for adhesives (epoxy/acrylate adhesives). Cured by visible light, for example Toyo Ink Mfg. Co., JP7082546 and JP7082544 (17 Sep. 1993).

Ketocoumarins have been used as photosensitizers with Amino-alkylphenones (Irgacure 369/379 type materials), for example Ciba EP1410109 (and family of patents) (26 Jul. 2001).

A recent patent by Fuji (EP2388146—19 May 2010) on LED curable inks and coatings for offset printing mentions the use of ketocoumarins as sensitizers for some new materials that they have developed (general structure shown below). Their new materials appear to be used as photoinitiators/sensitizers in combination with, in particular, aminoalkylphenones and acylphosphine oxides. There are no claims about the use of coumarins but they are mentioned as possible sensitizers in the main body of the patent.

Other areas where certain types of ketocoumarins have been patented (synthesis and use) are: As dyes/filter dyes and Photoimaging technology, for example Sandoz, GB1509386 (3 Jul. 1974); Hoechst EP0044026 (11 Jul. 1980); ICI, GB1405177 (26 Apr. 1972); Mead Corp., U.S. Pat. No. 4,713,312 and CA1293407 (9 Oct. 1984), JP2191956 (21 Nov. 1988); Brother Ind. Ltd., JP8220746 and JP3185585 (16 Feb. 1995); Nippon Kanko Shikiso Kenkyusho, JP7316147 and JP3554363 (26 May 1995); Konishiroku Photo. Ind., JP2000275827 (29 Mar. 1999).

Ketocoumarins have been used as fluorescent labeling agents, for example Biocarb AB, U.S. Pat. No. 4,956,480 (3 Dec. 1985).

Ketocoumarins have been used in Pharmacological applications, for example Cassella Farbwerke Mainkur AG, GB1014053 (12 Aug. 1961); Hardman and Holden Ltd., GB911632 (7 Sep. 1959); Beecham Group Ltd., GB1307646 (31 Oct. 1969).

None of the prior art references disclose the ketocoumarins of the present invention and their use as described below.

SUMMARY OF THE INVENTION

The present invention provides compound of formula (I):

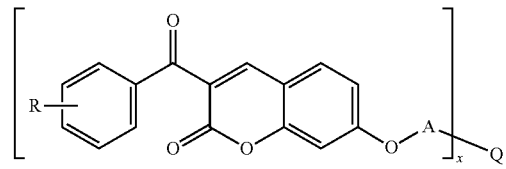

where:
R is an alkyl or alkoxy substituents;
$A = -CH_2-R^1-(CH_2)_n-[O(CHR^2CHR^3)_a]_y-$, where
  n=0 or 1
  a=1 to 2
  $R^1 = -C=O$ or $-CH(OH)-$
  y=0 to 10,
  one of $R^2$ and $R^3$ represents a hydrogen atom and the other represents a hydrogen atom, methyl group or ethyl group;
Q is a residue selected from the group consisting of; monohydroxy compounds having from 1 to 6 hydroxy groups, polyhydroxy compounds having from 1 to 6 hydroxy groups, and $C_2$-$C_{12}$ polyalkylene glycols in which the alkylene part has from 2 to 12 carbon atoms; and
x is an integer from 1 to 6.

When x=1, the present invention provides a compound according to formula (I), where
Q is a residue selected from the group consisting of a compound of formula $R^4-OH$, where $R^4$ is a $C_1$ to $C_{12}$ alkyl group, and a group of formula $-[O(CHR^2CHR^3)_a]_y-OCH_3$, where a is a number from 1-2, y is a number from 0 to 10, and $R^2$ and $R^3$ are the same or different and each represents a hydrogen atom or a $C_1$-$C_4$ alkyl group.

It will be appreciated that, when the compounds of the present invention are analyzed, the numbers a and y in the above formula need not be integers, and, indeed, it is unlikely that they will be integers, since the compounds of the present invention may be mixtures of several compounds in which the numbers a and y differ. In accordance with the present invention, provided that the average value of each of these numbers is as defined above, this will be satisfactory. Of course, for each individual molecule of the compounds of the present invention, a and y will be integers, and it might be possible to separate out such individual compounds, but in practice, mixtures of these compounds are typically used.

The present invention also provides a radiation-curable composition (e.g. printing ink, coating, varnish, adhesive, etc.) comprising the compound of formula (I) above.

The present invention also provides a method of preparing a cured polymeric composition comprising exposing a radiation curable coating composition containing the compound of formula (I) to actinic radiation.

The present invention also provides a method of preparing a radiation curable composition comprising combining the compound of claim 1 with one or more materials selected from the group consisting of polymerizable monomers, prepolymers, oligomers, other photoinitiators, an amine synergist and a sensitizer.

The present invention also provides a radiation curable ink, coating, varnish or adhesive suitable for food packaging, comprising the compound of formula (I).

DETAILED DESCRIPTION OF THE INVENTION

The present invention relates to a series of novel ketocoumarin photoinitiators for use in radiation curing, for example in the radiation curing of coating compositions such as printing inks or varnishes. Typical areas where these materials could be used are offset, flexo, inkjet, gravure, intaglio and screen where the inks/coatings are cured by UV radiation. The novel ketocoumarins of the present invention exhibit good reactivity, improved solubility and good print properties compared to existing materials of this type.

The ketocoumarins of the present invention have the compound of formula (I):

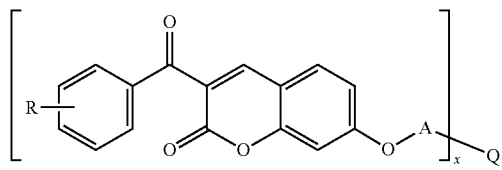

where:
R is an alkyl or alkoxy substituents;
A=—$CH_2$—$R^1$—$(CH_2)_n$—$[O(CHR^2CHR^3)_a]_y$—, where
n=0 or 1
a=1 to 2
$R^1$=—C=O or —CH(OH)—
y=0 to 10,
one of $R^2$ and $R^3$ represents a hydrogen atom and the other represents a hydrogen atom, methyl group or ethyl group;
Q is a residue selected from the group consisting of; monohydroxy compounds having from 1 to 6 hydroxy groups, polyhydroxy compounds having from 1 to 6 hydroxy groups, and $C_2$-$C_{12}$ polyalkylene glycols in which the alkylene part has from 2 to 12 carbon atoms; and
x is an integer from 1 to 6.

In a preferred embodiment, Q is a residue of polyhydroxy compounds selected from the group consisting of; ethylene glycol, propylene glycol, butylene glycol, glycerol, 2,2-propanediol, polyethylene glycol, polypropylene glycol, polybutylene glycol, trimethylolpropane, di-trimethylolpropane, pentaerythritol and di-pentaerythritol.

In another preferred embodiment, Q is a residue of monohydroxy compounds selected from the group consisting of; a compound of formula $R^4$—OH where $R^4$ is a $C_1$ to $C_{12}$ alkyl group and a group of formula —$[O(CHR^2CHR^3)_a]_y$—$OCH_3$ where a is a number from 1-2, y is a number from 0 to 10, and $R^2$ and $R^3$ are the same or different and each represents a hydrogen atom or a $C_1$-$C_4$ alkyl group.

In another preferred embodiment, Q is a residue of polyalkylene glycols selected from the group consisting of; butane-1,4-diol, hexane-1,6-diol, octane-1,8-diol, decane-1,10-diol and dodecane-1,12-diol.

The novel materials would preferably be used in printing inks, coatings, varnishes and adhesives because of their improved solubility. In a preferred embodiment, the novel materials would be used in printing inks and coatings, especially offset inks and inkjet inks. The improved solubility compared to existing ketocoumarin materials will therefore give improved print properties. Some of the materials developed could also be considered for use in low-migration technology used in food packaging applications.

In a commercial environment, curing of inks and coatings is carried out by using medium pressure mercury arc lamps. However, in recent years, there have been many new developments in this area and it is preferable that photoinitiators are also capable of working with some, or all of these new curing sources, which typically emit at longer wavelengths than standard medium pressure mercury lamps. Examples of these new light sources include iron-doped mercury lamps, such as those used in the Komori H-UV systems; gallium-doped lamps, such as those that are recommended for curing of white inks; and LED lamps of various emitting wavelengths.

The compounds that are the basis of the present invention all have shifted chromophores as a result of the oxygen attached to the ketocoumarins ring structure, which preferably pushes the absorption maximum out to around 344 nm and extends up to 400 nm. The significant absorption at 365 nm, which is the strongest emission wavelength of the commonly used medium pressure mercury arc lamp is also preferred, and means that the compounds of the present invention are effective photoinitiators with a wide range of UV lamp types; from the most common medium pressure mercury arc lamp to the newest types with dope metal additives. In addition, the preferred absorption maximum for these photoinitiators sits in the wavelength region between those of commonly used photoinitiators such as benzophenone, phenylbenzophenone and Irgacure 369, which all have peak maximum in the range 250-325 nm, and 2-isopropyl thioxanthone with its peak maximum at 384 nm. As a result, the photoinitiators of the present invention are an ideal formulating tool to make photoinitiator blends with other materials and provide a balanced absorption of light right through the important UV curing wavelengths 200-450 nm.

The materials have been designed so that ketocoumarin functional photoinitiators have been obtained with good cure performance. The use of the hydroxy ketocoumarin (Inventive Example 1) is an important intermediate in the synthesis of the novel materials. The materials exhibit improved solubility compared to previous materials of this type which means they can be used in inks and coatings without detracting from the print properties of the inks/coatings.

A range of novel ketocoumarin photoinitiators have been synthesized. The use of synthetic chemistry routes, such as esterification and formation of ether links by substitution reactions or ring opening of epoxides, to link initiator moieties to a multifunctional core or other functional groups that could improve solubility, can be used to produce these novel materials. The novel materials have been evaluated in inkjet and offset inks, and also for use in ink and coating formulations that are cured with H-UV lamps (e.g. Komori Corp.) by directly replacing the current commercial photoinitiators. The evaluations indicate that the best of the novel materials are performing as well as the current commercial materials.

The novel ketocoumarin photoinitiators of the present invention exhibit improved solubility, which therefore gives improved print properties and good reactivity. These have not previously been reported in the literature.

The compositions of the present invention may be incorporated into a printing ink, varnish, adhesive or any other coating composition which is intended to be cured by irradiation, for example ultraviolet, electron beam, etc. Such compositions will typically contain at least a polymerizable monomer, prepolymer or oligomer; a photoinitiator of the present invention; an amine synergist; and optionally a sensitizer; but may also include other components well known to those skilled in the art, for example, waxes, flow aids and other additives, and in the case of printing inks, colorants.

Suitable colorants include, but are not limited to organic or inorganic pigments and dyes. The dyes include but are not limited to azo dyes, anthraquinone dyes, xanthene dyes, azine dyes, combinations thereof and the like. Organic pigments may be one pigment or a combination of pigments, such as for instance Pigment Yellow Numbers 12, 13, 14, 17, 74, 83, 114, 126, 127, 174, 188; Pigment Red Numbers 2, 22, 23, 48:1, 48:2, 52, 52:1, 53, 57:1, 112, 122, 166, 170, 184, 202, 266, 269; Pigment Orange Numbers 5, 16, 34, 36; Pigment Blue Numbers 15, 15:3, 15:4; Pigment Violet Numbers 3, 23, 27; and/or Pigment Green Number 7. Inorganic pigments may be one of the following non-limiting pigments: iron oxides, titanium dioxides, chromium oxides, ferric ammonium ferrocyanides, ferric oxide blacks, Pigment Black Number 7 and/or Pigment White Numbers 6 and 7. Other organic and inorganic pigments and dyes can also be employed, as well as combinations that achieve the colors desired.

A wide variety of monomers and prepolymers may be subjected to photoinitiation with the photoinitiators of the present invention, and the nature of the monomers and prepolymers is not critical to the present invention.

The present invention has been described in detail, including the preferred embodiments thereof. However, it will be appreciated that those skilled in the art, upon consideration of the present disclosure, may make modifications and/or improvements on this invention that fall within the scope and spirit of the invention.

The following examples illustrate specific aspects of the present invention and are not intended to limit the scope thereof in any respect and should not be so construed.

Comparative Example 1

Prior Art Ketocoumarins

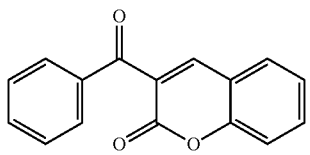 [SMILES: O=C(c1ccccc1)c1cc2ccccc2oc1=O]

61.0 g salicylaldehyde (0.5 moles), 96.0 g ethylbenzoyl acetate (0.5 moles) and 2.0 g of piperidine were mixed in 800 ml of ethanol. The mixture was heated to reflux for 6 hours and then cooled overnight to crystallize the product. The product was collected by filtration and recrystallized from ethanol and then dried in air to yield the solid product.

The yield was 104 g (83.2%).

The product was analyzed by NMR and HPLC.

Comparative Example 2

Prior Art Ketocoumarins

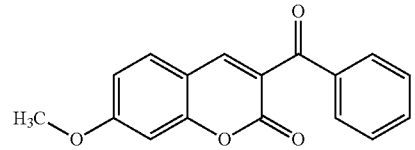 [SMILES: COc1ccc2cc(C(=O)c3ccccc3)c(=O)oc2c1]

15.2 g 2-hydroxy-4-methoxybenzaldehyde (0.1 moles), 19.2 g ethylbenzoyl acetate (0.1 moles) and 3.8 g of piperidine were mixed in 200 ml of ethanol. The mixture was heated to reflux for 3 hours and then cooled overnight to crystallize the product. The product was collected by filtration and recrystallized from ethanol and then dried in air to yield the solid product.

The yield was 22.3 g (79.6%).

The product was analyzed by NMR and HPLC.

Inventive Example 1

Intermediate

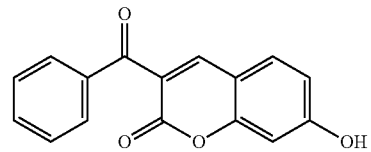 [SMILES: O=C(c1ccccc1)c1cc2ccc(O)cc2oc1=O]

60.0 g 2,4-dihydroxybenzaldehyde (0.435 moles), 83.49 g ethylbenzoyl acetate (0.435 moles) and 1.5 g of piperidine were mixed in 600 ml of ethanol. The mixture was heated to reflux for 6 hours and then cooled overnight to crystallize the product. The product was collected by filtration and recrystallized from ethanol and then dried in an oven at 50° C. to yield the solid product.

The yield was 93.45 g (80.77%).

The product was analyzed by NMR and HPLC.

Inventive Example 2

Intermediate

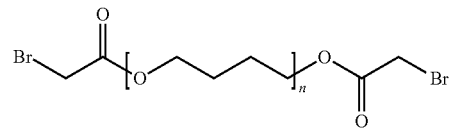

22.90 g bromoacetic acid (0.165 moles) and 18.75 g polytetrahydrofuran250 (Terathane® 250) (0.075 moles) were azeotropically refluxed for 7 hours in 50 ml toluene using 0.375 g p-toluenesulphonic acid as a catalyst and 0.075 g butylated hydroxytoluene as a stabilizer. The solution was cooled and washed with 100 ml of 10% potassium carbonate solution and then with water until the washings were neutral (pH7). The organic phase was then dried with anhydrous magnesium sulphate and the solvent removed in a rotary evaporator to yield a low viscosity clear liquid.

The yield was =35.75 g (96.9%)

The product was analyzed by IR.

IR: 1730-1740 cm$^{-1}$ C=O (strong) due to ester. No OH peak present.

Inventive Example 3

Finished Ketocoumarin Synthesis

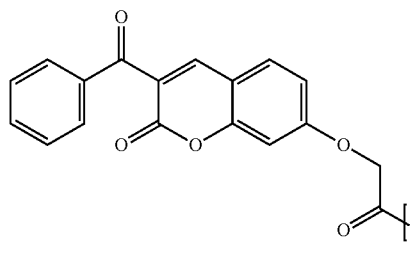

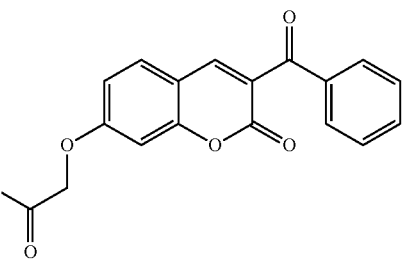

14.0 g (0.0526 moles) of the product from Inventive Example 1, 9.1 g of potassium carbonate (0.0658 moles) and 90 ml of methyl ethyl ketone were heated to reflux for 5 hours. The mixture was cooled to room temperature and 12.95 g of the product from Inventive Example 2 was added and the mixture heated to reflux for 7 hours. The mixture was cooled to room temperature and 150 ml of dichloromethane was added. The mixture was extracted with 100 ml of 0.5M sodium hydroxide aqueous solution and then twice with 150 ml of water. The organic phase was dried with anhydrous magnesium sulphate and then the solvent was removed to yield the product as a pasty brown solid.

28.804 g bromoacetic acid (0.2073 moles) and 10.00 g diethylene glycol (0.09423 moles) were azeotropically refluxed for 7 hours in 50 ml toluene using 0.33 g p-toluenesulphonic acid as a catalyst and 0.07 g butylated hydroxytoluene as a stabilizer. The solution was cooled and washed with 100 ml of 10% potassium carbonate solution and then with water until the washings were neutral (pH7). The organic phase was then dried with anhydrous magnesium sulphate and the solvent removed in a rotary evaporator to yield a low viscosity clear liquid.

The yield was =29.57 g (90.2%)

The product was analyzed by IR.

IR: 1730-1740 cm$^{-1}$ C=O (strong) due to ester. No OH peak present.

Inventive Example 5

Finished Ketocoumarin Synthesis

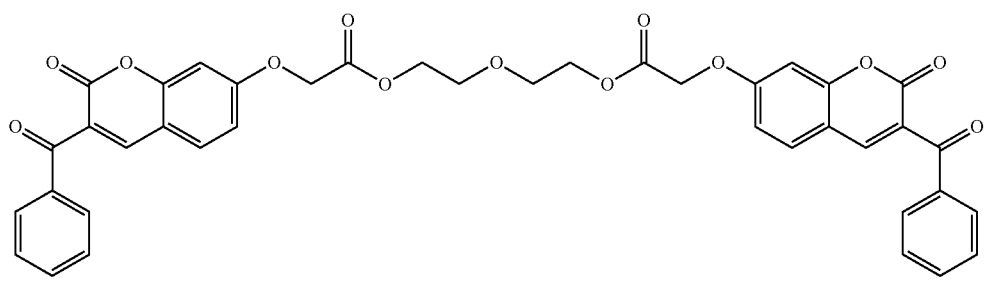

The yield was =16.0 g (61.75%)

The product was analyzed by NMR and HPLC.

Inventive Example 4

Intermediate

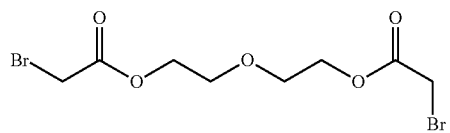 [SMILES: O=C(CBr)OCCOCCOC(=O)CBr]

3.0 g (0.01128 moles) of the product from Inventive Example 1, 1.95 g of potassium carbonate (0.0141 moles) and 30 ml of methyl ethyl ketone were heated to reflux for 5 hours. The mixture was cooled to room temperature and 1.963 g of the product from Inventive Example 4 was added and the mixture heated to reflux for 7 hours. The mixture was cooled to room temperature and 100 ml of dichloromethane was added. The mixture was extracted with 75 ml of 0.5M sodium hydroxide aqueous solution and then twice with 100 ml of water. The organic phase was dried with anhydrous magnesium sulphate and then the solvent was removed to yield the product as a light brown solid.

The yield was 3.27 g (80.75%).

The product was analyzed by NMR and HPLC.

Inventive Example 6

Intermediate

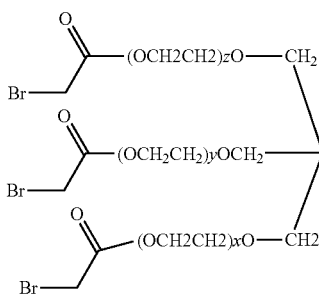

13.89 g bromoacetic acid (0.1 moles) and 12.5 g Polyol DPP130® (ex Perstorp) (0.015125 moles) were azeotropically refluxed for 7 hours in 50 ml toluene using 0.225 g p-toluenesulphonic acid as a catalyst and 0.045 g butylated hydroxytoluene as a stabilizer. The solution was cooled and washed with 75 ml of 10% potassium carbonate solution and then with water until the washings were neutral (pH7). The organic phase was then dried with anhydrous magnesium sulphate and the solvent removed in a rotary evaporator to yield a low viscosity clear liquid.

The yield was =11.8 g (50.3%)

The product was analyzed by IR.

IR: 1730-1740 cm$^{-1}$ C=O (strong) due to ester. No OH peak present.

Inventive Example 7

Finished Ketocoumarin Synthesis

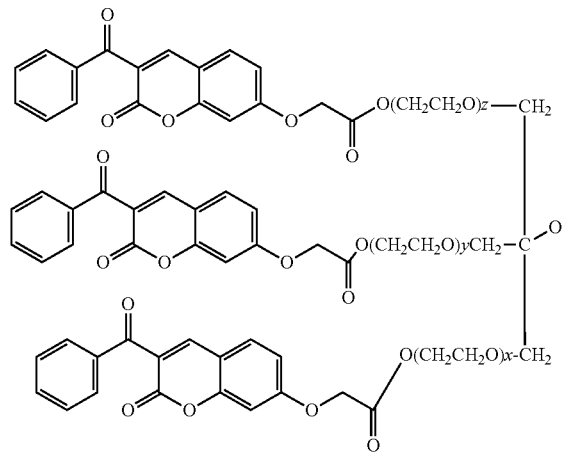

5.144 g (0.01934 moles) of the product from Inventive Example 1, 3.34 g of potassium carbonate (0.02417 moles) and 30 ml of methyl ethyl ketone were heated to reflux for 5 hours. The mixture was cooled to room temperature and 5.0 g of the product from Inventive Example 6 were added and the mixture heated to reflux for 7 hours. The mixture was cooled to room temperature and 100 ml of dichloromethane was added. The mixture was extracted with 75 ml of 0.5M sodium hydroxide aqueous solution and then twice with 100 ml of

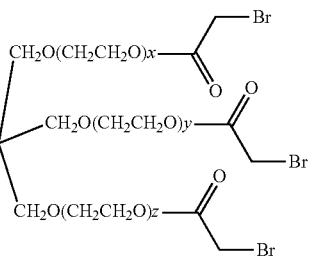

water. The organic phase was dried with anhydrous magnesium sulphate and then the solvent was removed to yield the product as a yellow solid.

The yield was 7.00 g (81.6%).

The product was analyzed by NMR and HPLC.

Inventive Example 8

Intermediate

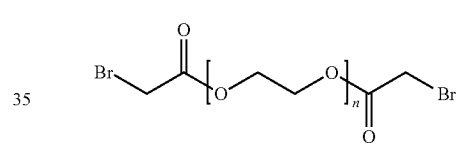

11.46 g bromoacetic acid (0.0825 moles) and 15.0 g Polyethylene glycol 400 (0.0375 moles) were azeotropically

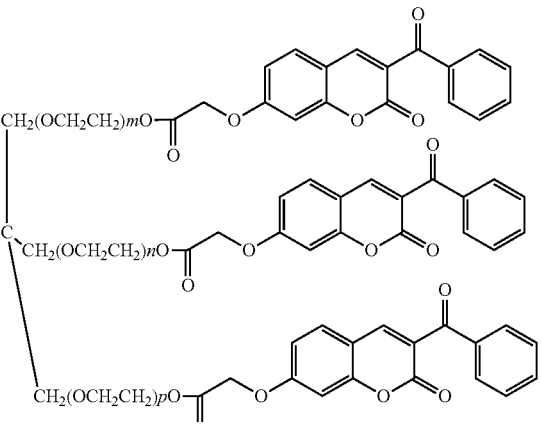

refluxed for 7 hours in 50 ml toluene using 0.25 g p-toluenesulphonic acid as a catalyst and 0.03 g butylated hydroxytoluene as a stabilizer. The solution was cooled and washed with 75 ml of 10% potassium carbonate solution and then with water until the washings were neutral (pH7). The organic phase was then dried with anhydrous magnesium sulphate and the solvent removed in a rotary evaporator to yield a low viscosity clear liquid.

The yield was =12.7 g (52.8%)

The product was analyzed by IR.

IR: 1730-1740 cm$^{-1}$ C=O (strong) due to ester. No OH peak present.

Inventive Example 9

Finished Ketocoumarin Synthesis

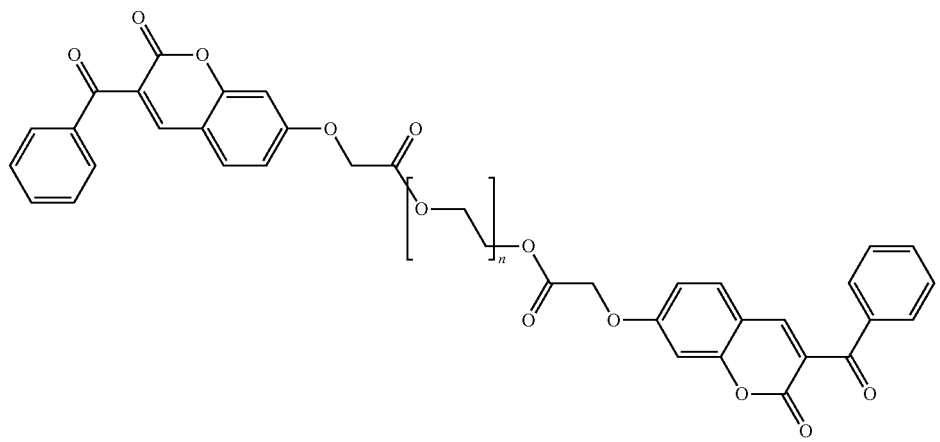

4.145 g (0.01558 moles) of the product from Inventive Example 1, 2.69 g of potassium carbonate (0.01946 moles) and 30 ml of methyl ethyl ketone were heated to reflux for 5 hours. The mixture was cooled to room temperature and 5.0 g of the product from Inventive Example 8 was added and the mixture heated to reflux for 7 hours. The mixture was cooled to room temperature and 100 ml of dichloromethane was added. The mixture was extracted with 75 ml of 0.5M sodium hydroxide aqueous solution and then twice with 100 ml of water. The organic phase was dried with anhydrous magnesium sulphate and then the solvent was removed to yield the product as a yellow/brown viscous liquid.

The yield was 6.60 g (83.7%).

The product was analyzed by NMR and HPLC.

Inventive Example 10

Intermediate

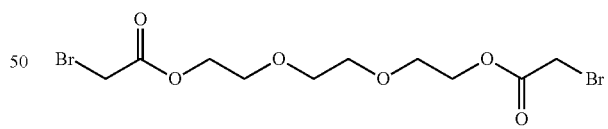

15.26 g bromoacetic acid (0.10987 moles) and 7.5 g Triethylene glycol (0.0499 moles) were azeotropically refluxed for 7 hours in 50 ml toluene using 0.25 g p-toluenesulphonic acid as a catalyst and 0.03 g butylated hydroxytoluene as a stabilizer. The solution was cooled and washed with 75 ml of 10% potassium carbonate solution and then with water until the washings were neutral (pH7). The organic phase was then dried with anhydrous magnesium sulphate and the solvent removed in a rotary evaporator to yield a low viscosity clear brown liquid.

The yield was =10.8 g (55.16%)

The product was analyzed by IR.

IR: 1730-1740 cm$^{-1}$ C=O (strong) due to ester. No OH peak present.

Inventive Example 11

Finished Ketocoumarin Synthesis

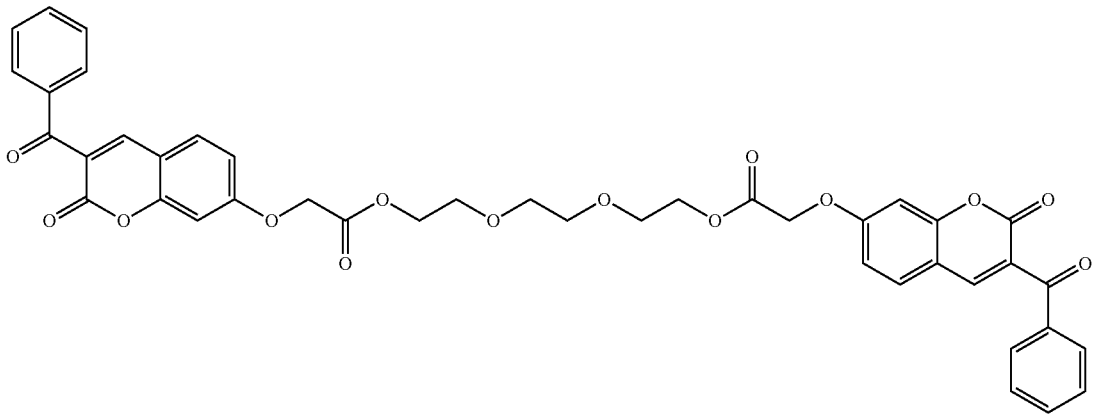 [SMILES: O=C(COc1ccc2cc(C(=O)c3ccccc3)c(=O)oc2c1)OCCOCCOCCOC(=O)COc1ccc2cc(C(=O)c3ccccc3)c(=O)oc2c1]

6.786 g (0.0255 moles) of the product from Inventive Example 1, 4.41 g of potassium carbonate (0.0319 moles) and 30 ml of methyl ethyl ketone were heated to reflux for 5 hours. The mixture was cooled to room temperature and 5.0 g of the product from Inventive Example 10 were added and the mixture heated to reflux for 7 hours. The mixture was cooled to room temperature and 100 ml of dichloromethane was added. The mixture was extracted with 75 ml of 0.5M sodium hydroxide aqueous solution and then twice with 100 ml of water. The organic phase was dried with anhydrous magnesium sulphate and then the solvent was removed to yield the product as a pink solid.

The yield was 7.0 g (72.0%).

The product was analyzed by NMR and HPLC.

Inventive Example 12

Finished Ketocoumarin Synthesis

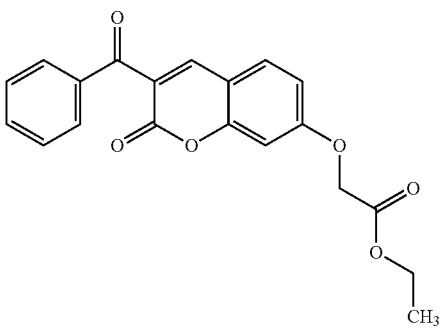 [SMILES: CCOC(=O)COc1ccc2cc(C(=O)c3ccccc3)c(=O)oc2c1]

7.964 g (0.02994 moles) of the product from Inventive Example 1, 5.0172 g of potassium carbonate (0.0374 moles) and 50 ml of methyl ethyl ketone were heated to reflux for 5 hours. The mixture was cooled to room temperature and 5.0 g of ethyl bromoacetate (0.02994 moles) were added and the mixture heated to reflux for 7 hours. The mixture was cooled to room temperature and 200 ml of water and 300 ml of dichloromethane were added and the mixture separated. The organic phase was extracted with a further 100 ml of water and then dried with anhydrous magnesium sulphate. The solvent was removed to yield the product as a white/light brown solid.

The yield was 5.58 g (52.9%).

The product was analyzed by NMR and HPLC.

Inventive Example 13

Intermediate

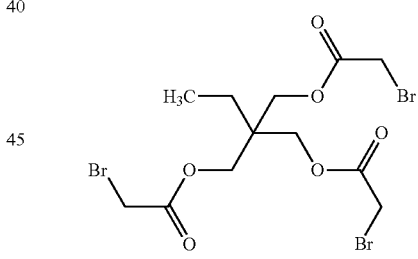

25.63 g bromoacetic acid (0.1845 moles) and 7.5 g Trimethylol propane (0.0559 moles) were azeotropically refluxed for 7 hours in 50 ml toluene using 0.25 g p-toluenesulphonic acid as a catalyst and 0.03 g butylated hydroxytoluene as a stabilizer. The solution was cooled and washed with 75 ml of 10% potassium carbonate solution and then with water until the washings were neutral (pH7). The organic phase was then dried with anhydrous magnesium sulphate and the solvent removed in a rotary evaporator to yield a low viscosity clear brown liquid.

The yield was 26.4 g (95.1%)

The product was analyzed by IR.

IR: 1730-1740 cm$^{-1}$ C=O (strong) due to ester. No OH peak present.

Inventive Example 14

Finished Ketocoumarin Synthesis

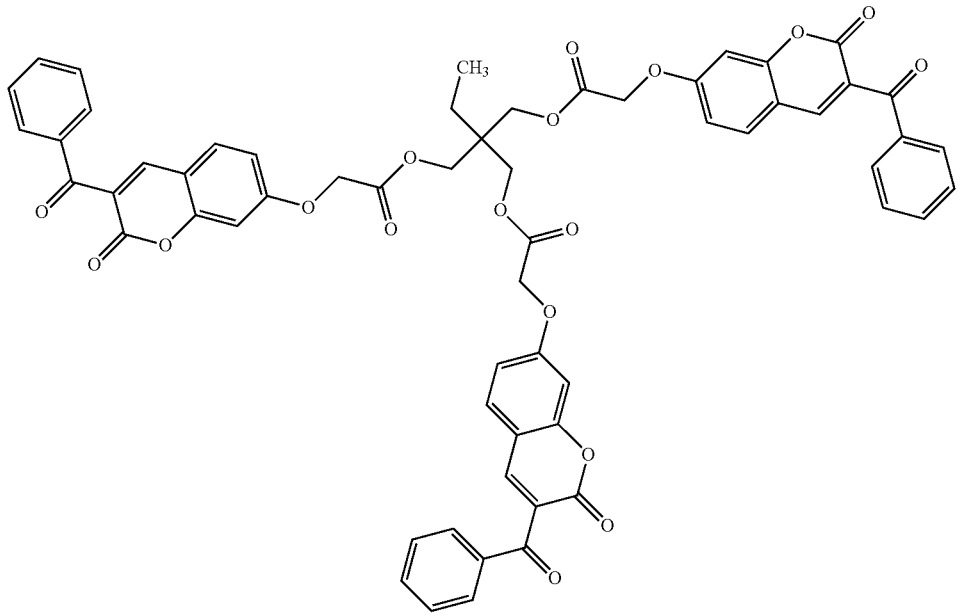 [SMILES: CCC(COC(=O)COc1ccc2cc(C(=O)c3ccccc3)c(=O)oc2c1)(COC(=O)COc1ccc2cc(C(=O)c3ccccc3)c(=O)oc2c1)COC(=O)COc1ccc2cc(C(=O)c3ccccc3)c(=O)oc2c1]

8.033 g (0.0302 moles) of the product from Inventive Example 1, 5.22 g of potassium carbonate (0.03777 moles) and 30 ml of methyl ethyl ketone were heated to reflux for 5 hours. The mixture was cooled to room temperature and 5.0 g of the product from Inventive Example 13 were added and the mixture heated to reflux for 7 hours. The mixture was cooled to room temperature and 100 ml of dichloromethane was added. The mixture was extracted with 75 ml of 0.5M sodium hydroxide aqueous solution and then twice with 100 ml of water. The organic phase was dried with anhydrous magnesium sulphate and then the solvent was removed to yield the product as a yellow solid.

The yield was 9.0 g (85.0%).

The product was analyzed by NMR and HPLC.

Inventive Example 15

Intermediate 8.2 g bromoacetic acid (0.059 moles) and 10.0 g Dodecanol (0.05367 moles) were azeotropically refluxed for 7 hours in 50 ml toluene using 0.25 g p-toluenesulphonic acid as a catalyst and 0.03 g butylated hydroxytoluene as a stabilizer. The solution was cooled and washed with 75 ml of 10% potassium carbonate solution and then with water until the washings were neutral (pH7). The organic phase was then dried with anhydrous magnesium sulphate and the solvent removed in a rotary evaporator to yield a low viscosity clear light brown liquid.

The yield was 16.5 g (100%)

The product was analyzed by IR.

IR: 1730-1740 cm$^{-1}$ C=O (strong) due to ester. No OH peak present.

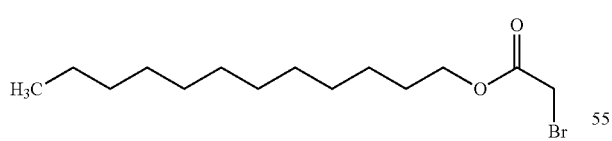

Inventive Example 16

Finished Ketocoumarin Synthesis

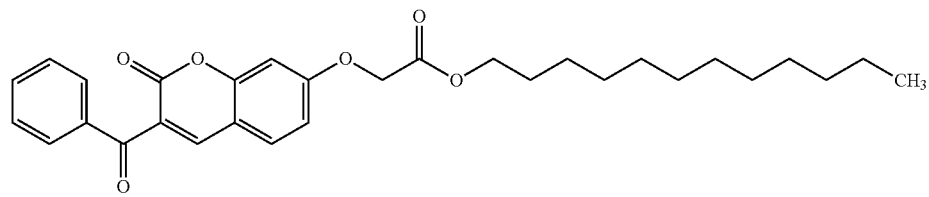 [SMILES: CCCCCCCCCCCCOC(=O)COc1ccc2cc(C(=O)c3ccccc3)c(=O)oc2c1]

4.33 g (0.01628 moles) of the product from Inventive Example 1, 2.81 g of potassium carbonate (0.02033 moles) and 30 ml of methyl ethyl ketone were heated to reflux for 5 hours. The mixture was cooled to room temperature and 5.0 g of the product from Inventive Example 15 were added and the mixture heated to reflux for 7 hours. The mixture was cooled to room temperature and 100 ml of dichloromethane was added. The mixture was extracted with 100 ml of 0.5M sodium hydroxide aqueous solution and then twice with 100 ml of water. The organic phase was dried with anhydrous magnesium sulphate and then the solvent was removed to yield the product as a brown solid.

The yield was 6.30 g (78.6%).

The product was analyzed by NMR and HPLC.

Inventive Example 17

Intermediate

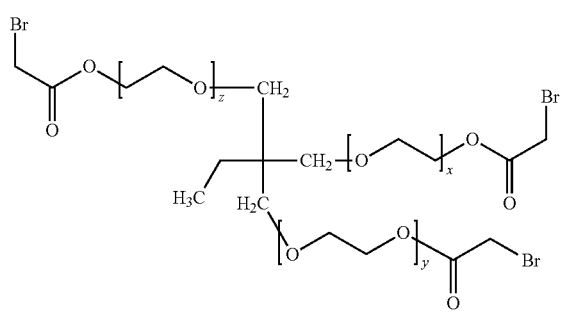

Where $x+y+z=3$ 15.21 g bromoacetic acid (0.1095 moles) and 7.5 g Polyol TP30® (ex Perstorp) (0.0282 moles) were azeotropically refluxed for 7 hours in 50 ml toluene using 0.25 g p-toluenesulphonic acid as a catalyst and 0.03 g butylated hydroxytoluene as a stabilizer. The solution was cooled and washed with 75 ml of 10% potassium carbonate solution and then with water until the washings were neutral (pH7). The organic phase was then dried with anhydrous magnesium sulphate and the solvent removed in a rotary evaporator to yield a low viscosity clear brown liquid.

The yield was 15.7 g (88.57%)

The product was analyzed by IR.

IR: 1730-1740 cm$^{-1}$ C=O (strong) due to ester. No OH peak present.

Inventive Example 18

Finished Ketocoumarin Synthesis

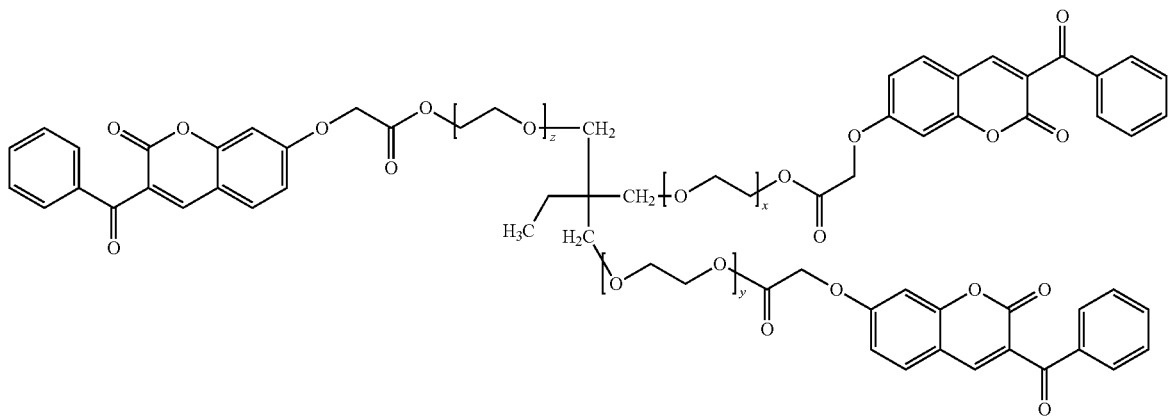

Where $x+y+z=3$ 6.35 g (0.02387 moles) of the product from Inventive Example 1, 4.12 g of potassium carbonate (0.0298 moles) and 30 ml of methyl ethyl ketone were heated to reflux for 5 hours. The mixture was cooled to room temperature and 5.0 g of the product from Inventive Example 17 were added and the mixture heated to reflux for 7 hours. The mixture was cooled to room temperature and 100 ml of dichloromethane was added. The mixture was extracted with 100 ml of 0.5M sodium hydroxide aqueous solution and then twice with 100 ml of water. The organic phase was dried with anhydrous magnesium sulphate and then the solvent was removed to yield the product as a light brown solid.

The yield was 6.70 g (71.15%).

The product was analyzed by NMR and HPLC.

Evaluation of Inventive Example 18 in Offset Inks

The performance of Inventive Example 18 was assessed in a black offset ink formulation and a yellow offset ink formulation. The inks were printed onto a carton board substrate (Incada Exel coated board from Iggesund) to a density of approximately 1.8-2.0 for the black inks and 0.9-1.1 for the yellow inks using an IGT C1 print proofer. These were cured using a Primarc UV rig fitted with a single 300 W/inch medium pressure mercury lamp. Prints of each of the inks were cured at four lamp power settings: 35 mJ, 49 mJ, 87 mJ and 115 mJ per pass. The number of passes required to cure was measured by a "set-off cure test" which is done by visually comparing the extent to which after each pass the ink has transferred to a piece of blank substrate under 10 tons pressure for 5 seconds. Decreased ink transfer is an indication of superior cure and hardness. The number of passes to achieve no set-off of cured ink onto a piece of blank substrate was recorded. The photoinitiator (PI) blends used for the evaluations are shown below.

Offset Black Ink A

Offset Black Ink A is based on a ketone functional resin, tri- and tetra-functional alkoxylated acrylates and approximately 14% carbon black pigment. Photoinitiator blends for Offset Black Ink A:

TABLE 1

| | Standard PI Blend A % | | Inventive PI Blend A % | | Inventive PI Blend B % |
|---|---|---|---|---|---|
| Omnipol BP | 6.1 | Inventive Ex. 18 | 6.8 | Inventive Ex. 18 | 8.0 |
| Irgacure 369 | 2.0 | Omnipol TX | 2.0 | Omnipol TX | 2.352 |
| Genopol AB1 | 2.7 | Genopol AB1 | 4.8 | Genopol AB1 | 5.648 |
| Omnipol TX | 5.2 | Irgacure 369 | 2.4 | Irgacure 369 | 0 |
| Total | 16.00 | Total | 16.00 | Total | 16.00 |

Offset Yellow Ink A

Offset Yellow Ink A is based on a ketone functional resin, tri- and tetra-functional alkoxylated acrylates and approximately 18% Yellow 13 pigment. Photoinitiator blends for Offset Yellow Ink A:

TABLE 2

| | Standard PI blend B % | | Inventive PI Blend C % | | Inventive PI Blend D % |
|---|---|---|---|---|---|
| Omnipol BP | 3.6 | Inventive Ex. 18 | 5.1 | Inventive Ex. 18 | 6.00 |
| Genopol AB1 | 5.6 | Omnipol TX | 1.5 | Omnipol TX | 1.764 |
| Omnipol TX | 1.6 | Genopol AB1 | 3.6 | Genopol AB1 | 4.236 |
| Irgacure 369 | 1.2 | Irgacure 369 | 1.8 | Irgacure 369 | 0 |
| Total | 12.00 | Total | 12.00 | Total | 12.00 |

The tables below show the results for the evaluations.

TABLE 3

Cure of Black and Yellow Offset Inks

| | | Cure Dose per pass (mJ) | | | |
|---|---|---|---|---|---|
| Ink Type | PI Blend used to cure Offset Black Ink 1 | 35 | 49 | 87 | 115 |
| | | Number of passes to cure | | | |
| Offset Black Ink A | Standard PI Blend A | 2 | 1 | 1 | 1 |
| Offset Black Ink A | Inventive PI Blend A | 2 | 1 | 1 | 1 |
| Offset Black Ink A | Inventive PI Blend B | 2 | 1 | 1 | 1 |
| Offset Yellow Ink A | Standard PI Blend B | 2 | 1 | 1 | 1 |
| Offset Yellow Ink A | Inventive PI Blend C | 2 | 1 | 1 | 1 |
| Offset Yellow Ink A | Inventive PI Blend D | 2 | 1 | 1 | 1 |

From the results obtained, it is clear that the inventive PI blends (which contain Inventive Example 18) perform as well as the standard PI blends in the black ink and yellow ink formulations for cure.

Inventive Example 19

Intermediate

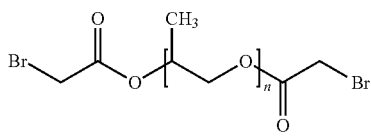

9.17 g bromoacetic acid (0.066 moles) and 12.75 g polypropylene glycol 425 (0.03 moles) were azeotropically refluxed for 7 hours in 50 ml toluene using 0.25 g p-toluenesulphonic acid as a catalyst and 0.03 g butylated hydroxytoluene as a stabilizer. The solution was cooled and washed with 75 ml of 10% potassium carbonate solution and then with water until the washings were neutral (pH7). The organic phase was then dried with anhydrous magnesium sulphate and the solvent removed in a rotary evaporator to yield a low viscosity clear brown liquid.

The yield was 18.0 g (100%)

The product was analyzed by IR.

IR: 1730-1740 $cm^{-1}$ C=O (strong) due to ester. No OH peak present.

Inventive Example 20

Finished Ketocoumarin Synthesis

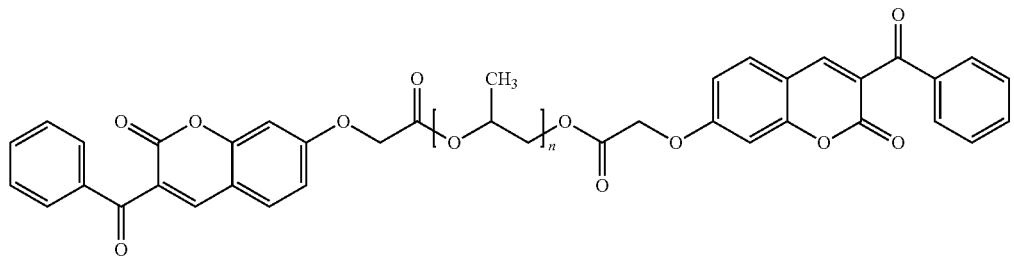

3.99 g (0.015 moles) of the product from Inventive example 1, 2.59 g of potassium carbonate (0.01874 moles) and 30 ml of methyl ethyl ketone were heated to reflux for 5 hours. The mixture was cooled to room temperature and 5.0 g of the product from Inventive Example 19 were added and the mixture heated to reflux for 7 hours. The mixture was cooled to room temperature and 100 ml of dichloromethane was added. The mixture was extracted with 100 ml of 0.5M sodium hydroxide aqueous solution and then twice with 100 ml of water. The organic phase was dried with anhydrous magnesium sulphate and then the solvent was removed to yield the product as a yellow viscous liquid.

The yield was 6.35 g (81.66%).

The product was analyzed by NMR and HPLC.

Inventive Example 21

Intermediate 4.7 g bromoacetic acid (0.0338 moles) and 15.0 g Boltorn H2004® (ex Perstorp—a dendritic polyol with a molecular weight of 3100 g/mol and 6 terminal hydroxy groups) (0.03075 moles of hydroxy functionality) were azeotropically refluxed for 7 hours in 50 ml toluene using 0.25 g p-toluenesulphonic acid as a catalyst and 0.03 g butylated hydroxytoluene as a stabilizer. The solution was cooled and washed with 75 ml of 10% potassium carbonate solution and then with water until the washings were neutral (pH7). The organic phase was then dried with anhydrous magnesium sulphate and the solvent removed in a rotary evaporator to yield a viscous clear brown liquid.

The yield was 13.7 g (74.5%)

The product was analyzed by IR.

IR: 1730-1740 cm$^{-1}$ C=O (strong) due to ester. No OH peak present.

Inventive Example 22

Finished Ketocoumarin Synthesis 2.033 g (0.007643 moles) of the product from Inventive example 1, 1.32 g of potassium carbonate (0.00955 moles) and 30 ml of methyl ethyl ketone were heated to reflux for 5 hours. The mixture was cooled to room temperature and 5.0 g of the product from Inventive Example 21 were added and the mixture heated to reflux for 7 hours. The mixture was cooled to room temperature and 100 ml of dichloromethane was added. The mixture was extracted with 100 ml of 0.5M sodium hydroxide aqueous solution and then twice with 100 ml of water. The organic phase was dried with anhydrous magnesium sulphate and then the solvent was removed to yield the product as a yellow/brown viscous liquid/paste.

The yield was 5.0 g (77.95%).

The product was analyzed by NMR and HPLC.

Inventive Example 23

Intermediate

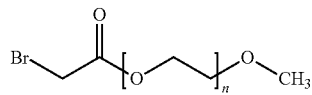

8.74 g bromoacetic acid (0.06286 moles) and 20.0 g polyethylene glycol 350 monomethylether (0.05714 moles) were azeotropically refluxed for 7 hours in 50 ml toluene using 0.25 g p-toluenesulphonic acid as a catalyst and 0.03 g butylated hydroxytoluene as a stabilizer. The solution was cooled and washed with 75 ml of 10% potassium carbonate solution and then with water until the washings were neutral (pH7). The organic phase was then dried with anhydrous magnesium sulphate and the solvent removed in a rotary evaporator to yield a low viscosity clear brown liquid.

The yield was 3.9 g (14.5%)

The product was analyzed by IR.

IR: 1730-1740 cm$^{-1}$ C=O (strong) due to ester. No OH peak present.

Example 24

Finished Ketocoumarin Synthesis

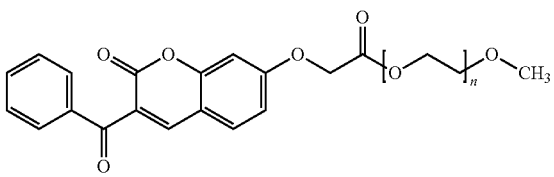

2.82 g (0.01060 moles) of the product from Inventive example 1, 1.83 g of potassium carbonate (0.01324 moles) and 30 ml of methyl ethyl ketone were heated to reflux for 5 hours. The mixture was cooled to room temperature and 5.0 g of the product from Inventive Example 23 were added and the mixture heated to reflux for 7 hours. The mixture was cooled to room temperature and 100 ml of dichloromethane was added. The mixture was extracted with 100 ml of 0.5M sodium hydroxide aqueous solution and then twice with 100 ml of water. The organic phase was dried with anhydrous magnesium sulphate and then the solvent was removed to yield the product as a yellow/brown viscous liquid.

The yield was 5.70 g (81.83%).

The product was analyzed by NMR and HPLC.

Inventive Example 25

Finished Ketocoumarin Synthesis

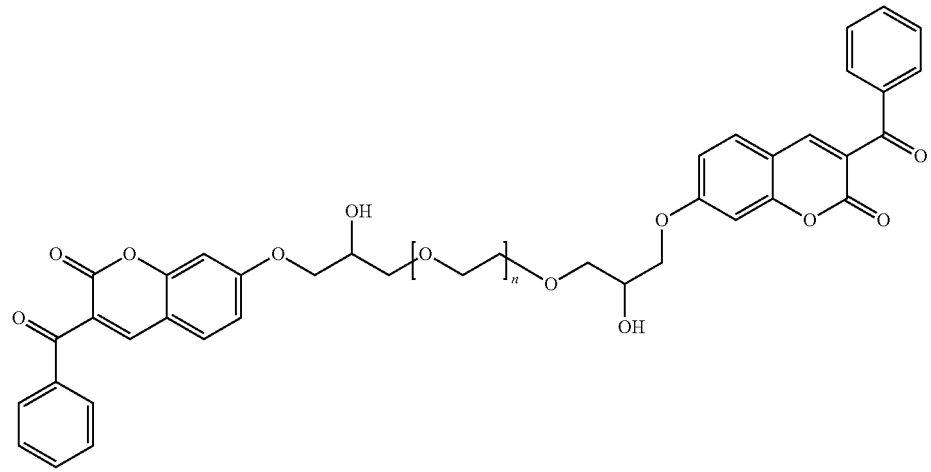

5.852 g (0.022 moles) of the product from Inventive Example 1, 5.26 g (0.01 moles) of polyethylene glycol 400 diglycidyl ether, 0.04 g of benzyl trimethyl ammonium chloride and 20 ml of toluene were mixed and heated to 100-110° C. for 20 hours. The mixture was then cooled and the toluene removed using a rotary evaporator. The residue was dissolved in 50 ml of dichloromethane and washed with 100 ml 1M sodium hydroxide aqueous solution and then with 2×100 ml of water. The organics were dried with anhydrous magnesium sulphate and then the solvent was removed to yield the product as an orange liquid.

The yield was 4.52 g (42.7%).

The product was analyzed by NMR and HPLC.

Example 26

Black Offset Inks

A series of 3 different black offset inks were prepared as follows to test the suitability of the ketocoumarins of the present invention.

Offset Black Ink 1—based on a urea-formaldehyde resin, trifunctional acrylate and approximately 13% carbon black pigment.

Photoinitiator Blends for Offset Black Ink 1

TABLE 4

| Standard PI Blend 1 | | Inventive PI Blend 1 | |
|---|---|---|---|
| 2-Ethylhexyl-4-Dimethylaminobenzoate | 6.40 | Ketocoumarin | 5.10 |
| Irgacure 369 | 2.49 | Omnipol TX | 1.50 |
| Methyl-o-benzoylbenzoate | 1.07 | Genopol AB1 | 3.60 |
| Phenyl benzophenone | 2.04 | Irgacure 369 | 1.80 |
| Total | 12.00 | Total | 12.00 |

The photoinitiator blends in Table 4 and the corresponding cure index results in Table 7 demonstrate how the inventive ketocoumarin photoinitiators of the present invention (Inventive PI Blend 1) perform in a blend with other low migration photoinitiators vs. a typical commercial photoinitiator blend (Standard PI Blend 1) that is not composed of low migration materials.

Offset Black Ink 2—based on a ketone functional resin, tri- and tetra-functional alkoxylated acrylates and approximately 14% carbon black pigment.

Photoinitiator Blends for Offset Black Ink 2

TABLE 5

| Standard PI Blend 2 | | Inventive PI Blend 2 | |
|---|---|---|---|
| Omnipol BP | 4.725 | Ketocoumarin | 5.10 |
| Irgacure 369 | 1.575 | Omnipol TX | 1.50 |

TABLE 5-continued

| Standard PI Blend 2 | | Inventive PI Blend 2 | |
|---|---|---|---|
| Genopol AB1 | 2.100 | Genopol AB1 | 3.60 |
| Omnipol TX | 3.600 | Irgacure 369 | 1.80 |
| Total | 12.00 | Total | 12.00 |

Offset Black Ink 3—based on a ketone functional resin, tri- and tetra-functional alkoxylated acrylates and approximately 14% carbon black pigment.

Photoinitiator Blends for Offset Black Ink 3

TABLE 6

| Standard PI blend 3 | | Inventive PI Blend 3 | |
|---|---|---|---|
| Omnipol BP | 5.44 | Ketocoumarin | 6.000 |
| Genopol AB1 | 2.42 | Omnipol TX | 1.764 |
| Omnipol TX | 4.14 | Genopol AB1 | 4.236 |
| Total | 12.00 | Total | 12.000 |

The inks were printed onto a carton board substrate (Incada Exel coated board from Iggesund) to a density of approximately 1.8-2.0 using an IGT C1 print proofer. These were cured at 100 m/min using a Primarc UV rig fitted with a single 300 W/inch medium pressure mercury lamp, operating at half power (~32 mJ per pass). The number of passes required to cure was measured by a "set-off cure test" which is done by visually comparing the extent to which after each pass the ink has transferred to a piece of blank substrate under 10 tons pressure for 5 seconds. Decreased ink transfer is an indication of superior cure and hardness. The amount of set-off is then measured using color computer software, which determines the average color density of the set-off ink compared to a blank piece of substrate. The amount of set-off is measured as the lightness "DL" of the blank substrate vs. the transferred ink film, measured using a Spectraflash 650 spectrophotometer. The DL value is measured for each pass of the ink underneath the curing lamp, using a fresh piece of substrate for each pass until the ink is deemed fully cured and there is no visible ink transfer. The cure index is calculated by adding the individual DL values and rounding the sum to the nearest whole number. For example, if 4 passes under the curing lamp was required to cure a given ink film, and the DL values for the first 3 passes were 8.89, 5.27, 2.15 respectively, then the sum of the figures would be 16.31, which would be rounded to a cure index of 16. Note that there is no DL value taken after the $4^{th}$ pass, as the ink film was determined to be fully cured by the visual absence of ink transferred during the set-off cure test. A lower cure index value is indicative of superior cure. The tables below show the results for the evaluations.

TABLE 7

Cure of Offset Black Ink 1

| Ink Type | PI Blend used to cure Offset Black Ink 1 | Ketocoumarin Synthesis Example used in Experimental PI blend | Cure index |
|---|---|---|---|
| Offset Black Ink 1 | Standard PI Blend 1 | — | 31 |
| Offset Black Ink 1 | Inventive PI Blend 1 | Comparative Example 1 | 28 |
| Offset Black Ink 1 | Inventive PI Blend 1 | Comparative Example 2 | 52 |
| Offset Black Ink 1 | Inventive PI Blend 1 | Inventive Example 3 | 31 |
| Offset Black Ink 1 | Inventive PI Blend 1 | Inventive Example 7 | 44 |
| Offset Black Ink 1 | Inventive PI Blend 1 | Inventive Example 9 | 38 |

TABLE 7-continued

Cure of Offset Black Ink 1

| Ink Type | PI Blend used to cure Offset Black Ink 1 | Ketocoumarin Synthesis Example used in Experimental PI blend | Cure index |
|---|---|---|---|
| Offset Black Ink 1 | Inventive PI Blend 1 | Inventive Example 11 | 53 |
| Offset Black Ink 1 | Inventive PI Blend 1 | Inventive Example 12 | 46 |
| Offset Black Ink 1 | Inventive PI Blend 1 | Inventive Example 14 | 28 |
| Offset Black Ink 1 | Inventive PI Blend 1 | Inventive Example 16 | 52 |
| Offset Black Ink 1 | Inventive PI Blend 1 | Inventive Example 18 | 36 |
| Offset Black Ink 1 | Inventive PI Blend 1 | Inventive Example 20 | 33 |
| Offset Black Ink 1 | Inventive PI Blend 1 | Inventive Example 22 | 51 |
| Offset Black Ink 1 | Inventive PI Blend 1 | Inventive Example 24 | 26 |
| Offset Black Ink 1 | Inventive PI Blend 1 | Inventive Example 25 | 29 |

TABLE 8

Cure of Offset Black Ink 2

| Ink Type | PI Blend used to cure Offset Black Ink 2 | Ketocoumarin Synthesis Example used in Experimental PI blend | Cure index |
|---|---|---|---|
| Offset Black Ink 2 | Standard PI Blend 2 | — | 22 |
| Offset Black Ink 2 | Inventive PI Blend 2 | Comparative Example 1 | 24 |
| Offset Black Ink 2 | Inventive PI Blend 2 | Comparative Example 2 | 13 |
| Offset Black Ink 2 | Inventive PI Blend 2 | Inventive Example 3 | 10 |
| Offset Black Ink 2 | Inventive PI Blend 2 | Inventive Example 7 | 11 |
| Offset Black Ink 2 | Inventive PI Blend 2 | Inventive Example 9 | 10 |
| Offset Black Ink 2 | Inventive PI Blend 2 | Inventive Example 11 | 23 |
| Offset Black Ink 2 | Inventive PI Blend 2 | Inventive Example 12 | 15 |
| Offset Black Ink 2 | Inventive PI Blend 2 | Inventive Example 14 | 7 |
| Offset Black Ink 2 | Inventive PI Blend 2 | Inventive Example 16 | 31 |
| Offset Black Ink 2 | Inventive PI Blend 2 | Inventive Example 18 | 13 |
| Offset Black Ink 2 | Inventive PI Blend 2 | Inventive Example 20 | 16 |
| Offset Black Ink 2 | Inventive PI Blend 2 | Inventive Example 22 | 25 |
| Offset Black Ink 2 | Inventive PI Blend 2 | Inventive Example 24 | 13 |
| Offset Black Ink 2 | Inventive PI Blend 2 | Inventive Example 25 | 19 |

TABLE 9

Cure of Offset Black Ink 3

| Ink Type | PI Blend used to cure Offset Black Ink 3 | Ketocoumarin Synthesis Example used in Experimental PI blend | Cure index |
|---|---|---|---|
| Offset Black Ink 3 | Standard PI Blend 3 | — | 47 |
| Offset Black Ink 3 | Inventive PI Blend 3 | Comparative Example 1 | 27 |
| Offset Black Ink 3 | Inventive PI Blend 3 | Comparative Example 2 | 33 |
| Offset Black Ink 3 | Inventive PI Blend 3 | Inventive Example 3 | 27 |
| Offset Black Ink 3 | Inventive PI Blend 3 | Inventive Example 7 | 23 |
| Offset Black Ink 3 | Inventive PI Blend 3 | Inventive Example 9 | 35 |
| Offset Black Ink 3 | Inventive PI Blend 3 | Inventive Example 11 | 42 |
| Offset Black Ink 3 | Inventive PI Blend 3 | Inventive Example 12 | 26 |
| Offset Black Ink 3 | Inventive PI Blend 3 | Inventive Example 14 | 14 |
| Offset Black Ink 3 | Inventive PI Blend 3 | Inventive Example 16 | 56 |
| Offset Black Ink 3 | Inventive PI Blend 3 | Inventive Example 18 | 34 |
| Offset Black Ink 3 | Inventive PI Blend 3 | Inventive Example 20 | 37 |
| Offset Black Ink 3 | Inventive PI Blend 3 | Inventive Example 22 | 46 |
| Offset Black Ink 3 | Inventive PI Blend 3 | Inventive Example 24 | 38 |
| Offset Black Ink 3 | Inventive PI Blend 3 | Inventive Example 25 | 57 |

From the results obtained, it is clear that many of the inventive materials perform as well as or better than standard photoinitiators in the black ink formulations for cure. It should be noted that the cure index numbers are a representation of cure at a relatively low UV lamp dose compared to that used in a commercial application. A commercial application would use multiples of higher power lamps and all of the above formulations would perform adequately under these conditions. The experiments have been set up to highlight differences in cure and therefore have been carried out at relatively low cure dose. In the above experiments, an ink with a cure index of less than 100 would cure adequately using commercial lamp conditions. Inks with a cure index of much lower than 100 are, therefore, performing very well.

The solubility of the materials was assessed by visual inspection of the inks and from visual inspection of the prints.

Insolubility is reported as follows: Good=Soluble (no solid bits in the ink and good printability); OK=Partially insoluble (some solid bits in the ink and slightly poor printability); Poor=Very noticeable insolubility (very noticeable solid bits in the ink and poor printability).

TABLE 10

Solubility Results

| Ketocoumarin Synthesis Example | Solubility in Offset Black Ink 1 | Solubility in Offset Black Ink 2 | Solubility in Offset Black Ink 3 |
|---|---|---|---|
| Comparative Example 1 | Poor | Poor | Poor |
| Comparative Example 2 | Poor | Poor | Poor |
| Inventive Example 3 | Good | Good | Good |
| Inventive Example 5 | Not evaluated | Not evaluated | Not evaluated |
| Inventive Example 7 | OK | OK | OK |
| Inventive Example 9 | OK | Good | Good |
| Inventive Example 11 | OK | OK | OK |
| Inventive Example 12 | OK | OK | OK |
| Inventive Example 14 | OK | OK | OK |
| Inventive Example 16 | OK | OK | OK |
| Inventive Example 18 | Good | Good | Good |
| Inventive Example 20 | Good | Good | Good |
| Inventive Example 22 | Good | Good | Good |
| Inventive Example 24 | Good | Good | Good |
| Inventive Example 25 | Good | Good | Good | diacrylate, dipropyleneglycol diacrylate, tripropylene glycol diacrylate (all at approximately 15%) and 2-(2-Vinyloxy-ethoxy)ethyl acrylate (at approximately 20%).

The photoinitiator (PI) blends used for the evaluations are shown below in Table 11:

TABLE 11

| Standard Ink-Jet PI Blend | | Inventive Ink-Jet PI Blend | |
|---|---|---|---|
| Amino Acrylate CN3715 | 4.667 | Amino Acrylate CN3715 | 4.667 |
| Genopol TX | 6.167 | Ketocoumarin | 6.167 |
| Irgacure 819/Irgacure 127 (50/50) | 6.167 | Irgacure 819/Irgacure 127 (50/50) | 6.167 |
| Total | 17.00 | Total | 17.00 |

The inks were printed onto white PE TopTrans top-coated label substrate using a No. 2 K-Bar (red). The No. 2 K-bar gives a film thickness of about 12 μm. The inks were cured at 70 m/min using a Primarc UV rig fitted with a single 300 W/inch medium pressure mercury lamp, operating at full power (84 mJ per pass). Cure index was determined using the same cure index test described above for the black offset inks.

Table 12 shows the results for the evaluations.

TABLE 12

Cure speed of Ink-Jet Magenta Inks

| Ink Type | PI Blend used to cure Ink-Jet Magenta Ink | Ketocoumarin Synthesis Example used in Experimental PI blend | Cure index |
|---|---|---|---|
| Ink-Jet Magenta | Standard Ink-Jet PI Blend | — | <1 |
| Ink-Jet Magenta | Inventive Ink-Jet PI Blend | Comparative Example 1 | 38 |
| Ink-Jet Magenta | Inventive Ink-Jet PI Blend | Comparative Example 2 | <1 |
| Ink-Jet Magenta | Inventive Ink-Jet PI Blend | Inventive Example 3 | 1 |
| Ink-Jet Magenta | Inventive Ink-Jet PI Blend | Inventive Example 5 | 9 |
| Ink-Jet Magenta | Inventive Ink-Jet PI Blend | Inventive Example 7 | <1 |
| Ink-Jet Magenta | Inventive Ink-Jet PI Blend | Inventive Example 9 | 3 |
| Ink-Jet Magenta | Inventive Ink-Jet PI Blend | Inventive Example 11 | 1 |
| Ink-Jet Magenta | Inventive Ink-Jet PI Blend | Inventive Example 12 | 3 |
| Ink-Jet Magenta | Inventive Ink-Jet PI Blend | Inventive Example 14 | 1 |
| Ink-Jet Magenta | Inventive Ink-Jet PI Blend | Inventive Example 16 | 5 |
| Ink-Jet Magenta | Inventive Ink-Jet PI Blend | Inventive Example 18 | 1.5 |
| Ink-Jet Magenta | Inventive Ink-Jet PI Blend | Inventive Example 20 | 2.5 |
| Ink-Jet Magenta | Inventive Ink-Jet PI Blend | Inventive Example 22 | 2.5 |
| Ink-Jet Magenta | Inventive Ink-Jet PI Blend | Inventive Example 24 | 3 |
| Ink-Jet Magenta | Inventive Ink-Jet PI Blend | Inventive Example 25 | 3 |

From the solubility evaluation it is clear that many of the novel materials described in the examples have much improved solubility in offset and ink-jet ink formulations compared to the materials described in the comparative examples. Improved solubility produces better reactivity and reduced print defect and reduced equipment failure.

Example 27

Ink-Jet Inks

Magenta ink-jet inks were prepared to assess the performance of the inventive ketocoumarin materials an ink-jet ink formulation. The magenta ink formulation is based on 17.5% of a magenta pigment concentrate and a blend of difunctional monomers which includes propoxylated neopentylglycol From the results obtained it is clear that many of the new materials are performing as well as photoinitiators in the comparative magenta ink-jet ink formulations for cure.

The cure index results in Table 12 were determined using the same test method as described for the black offset inks in Tables 7-9 with one exception; in Table 12 the cure index figures were rounded to the nearest 0.5 rather than to the nearest whole number. It should be noted that the cure index numbers are a representation of cure at a relatively low UV lamp dose compared to that used in a commercial application. A commercial application would typically use higher UV lamp dosage and all of the above formulations would perform adequately under these conditions. The experiments have been set up to highlight differences in cure and therefore have been carried out at relatively low cure dose. In the above experiments an ink with a cure index of less than 4-5 would cure adequately using commercial lamp conditions. Inks with a cure index of much lower than 4-5 are, therefore, performing very well.

The solubility of the materials was assessed by visual inspection of the inks and from visual inspection of the prints. Insolubility is reported as follows: Good=Soluble (no solid bits in the ink and good printability); OK=Partially insoluble (some solid bits in the ink and slightly poor printability); Poor=Very noticeable insolubility (very noticeable solid bits in the ink and poor printability).

TABLE 13

Solubility Results

| Ketocoumarin Synthesis Example | Solubility in Ink-Jet Magenta Ink |
|---|---|
| Comparative Example 1 | Poor |
| Comparative Example 2 | Poor |
| Inventive Example 3 | Good |
| Inventive Example 5 | Good |
| Inventive Example 7 | Poor |
| Inventive Example 9 | OK |
| Inventive Example 11 | OK |
| Inventive Example 12 | Poor |
| Inventive Example 14 | Poor |
| Inventive Example 16 | Poor |
| Inventive Example 18 | Good |
| Inventive Example 20 | Good |
| Inventive Example 22 | Good |
| Inventive Example 24 | Good |
| Inventive Example 25 | Good |

From the solubility evaluation it is clear that many of the novel materials described in the examples have much improved solubility in offset and ink-jet ink formulations compared to the materials described in the comparative examples. Improved solubility produces better reactivity and reduced print defect and reduced equipment failure.

Example 28

H-UV Lamps Curable Coating

A series of coatings suitable for curing with H-UV lamps were prepared to assess the performance of the inventive ketocoumarin materials.

A coating base was prepared with the following formulation:

TABLE 14

| Material | Weight % |
|---|---|
| Urethane acrylate oligomer | 33.34 |
| Trifunctional acrylate | 29.80 |
| Difunctional acrylate | 10.10 |
| Stabilizer | 0.29 |
| Defoamer | 0.20 |
| Slip additive | 1.67 |
| Total | 75.40 |

The following coating formulations were then prepared:

TABLE 15

| Material | Formulation number | | | | | | |
|---|---|---|---|---|---|---|---|
| | A | B | C | D | E | F | G |
| Coating base | 75.4 | 75.4 | 75.4 | 75.4 | 75.4 | 75.4 | 75.4 |
| Ebecryl P116 | 10.0 | 10.0 | 10.0 | 10.0 | 10.0 | 10.0 | 10.0 |

TABLE 15-continued

| | A | B | C | D | E | F | G |
|---|---|---|---|---|---|---|---|
| Inventive Example 3 | 6.0 | 2.0 | — | 2.0 | — | 2.0 | — |
| Irgacure 184 | — | 6.0 | 6.0 | — | — | — | — |
| Irgacure 651 | — | — | — | 6.0 | 6.0 | — | — |
| Omnirad TPO | — | — | — | — | — | 6.0 | 6.0 |
| Irgacure 369 | — | — | — | — | — | — | — |
| Omnipol BP | — | — | — | — | — | — | — |
| Omnirad ITX | — | — | — | — | — | — | — |
| TMPTA | 8.6 | 6.6 | 8.6 | 6.6 | 8.6 | 6.6 | 8.6 |
| Total | 100 | 100 | 100 | 100 | 100 | 100 | 100 |

| Material | Formulation number | | | | | |
|---|---|---|---|---|---|---|
| | H | I | J | K | L | M |
| Coating base | 75.4 | 75.4 | 75.4 | 75.4 | 75.4 | 75.4 |
| Ebecryl P116 | 10.0 | 10.0 | 10.0 | 10.0 | 10.0 | 10.0 |
| Inventive Example 3 | 2.0 | — | 2.0 | — | 2.0 | — |
| Irgacure 184 | — | — | — | — | — | — |
| Irgacure 651 | — | — | — | — | — | — |
| Omnirad TPO | — | — | — | — | — | — |
| Irgacure 369 | 6.0 | 6.0 | — | — | — | — |
| Omnipol BP | — | — | 6.0 | 6.0 | — | — |
| Omnirad ITX | — | — | — | — | 6.0 | 6.0 |
| TMPTA | 6.6 | 8.6 | 6.6 | 8.6 | 6.6 | 8.6 |
| Total | 100 | 100 | 100 | 100 | 100 | 100 |

The coating formulations were applied to Lenetta charts using a No. 0 K-bar (white) and cured using an H-UV lamp supplied by Baldwin and fitted to an IST curing rig. The H-UV lamp was operated at full power throughout. The coating formulations were given a single pass under the lamp at multiple line speeds and the fastest line speed which did not lead to a failure was recorded. Testing was by "thumb twist" and "finger tack". A failure for thumb twist is when the ink film mars or breaks when subjected to a medium pressure twist by thumb. A failure for finger tack is when the ink film exhibits discernible tack after curing. Acceptable cure is when the ink film passes both the thumb twist and finger tack tests. Prints were also assessed for color immediately after cure.

TABLE 16

| Formulation | Maximum line speed for acceptable cure (m/min) | Coating is yellow after cure? |
|---|---|---|
| A | 50 | No |
| B | 30 | No |
| C | <30 | No |
| D | 30 | No |
| E | <30 | No |
| F | 50 | No |
| G | 40 | No |
| H | 120 | Yes |
| I | 80 | Yes |
| J | 30 | No |
| K | 20 | No |
| L | 90 | Yes |
| M | 80 | Yes |

The results indicate that the novel photoinitiator from Inventive Example 3 can cure a simple coating using an H-UV lamp when used on its own or in combination with other photoinitiators.

Although the photoinitiators Irgacure 369 and Omnirad ITX have the best cure with H-UV lamps, their extent of yellowing during cure is very high, as is well known to those skilled in the art, and would make them disadvantageous for use in some coatings applications. The coating using the Example 3 of the current invention is however much less yellow and shows good reactivity in comparison to the other photoinitiators tested.

Example 29

Flexo Inks

A series of flexo inks were prepared to assess the performance of the inventive ketocoumarin materials in process yellow, magenta, cyan and black flexo ink formulations for a low migration product range. The inks were prepared according to the compositions below, where 50% of a technology varnish containing the photoinitiator system is blended with 50% of a pigment concentrate. An identical set of inks was prepared where the photoinitiator system did not contain the inventive photoinitiator substance.

TABLE 17

Flexo ink technology varnishes containing photoinitiator compositions

| Component | Source | (A) Standard Technology Varnish | (B) Inventive Technology Varnish |
| --- | --- | --- | --- |
| Omnipol TX | Low migration thioxanthone photoinitiator (IGM) | 4 | 2.5 |
| Irgacure 369 | Photoinitiator ex. BASF | 5 | 3.5 |
| Genopol 09-420 | Low migration amine synergist ex. Rahn | 8 | 6 |
| Omnipol BP | Low migration benzophenone photoinitiator (IGM) | 3.5 | — |
| Inv. Ex. 18 | | — | 8.5 |
| SR455LM | Trifunctional monomer ex. Sartomer | 50.46 | 50.46 |
| SR494LM | Tetrafunctional monomer from Sartomer | 15 | 15 |
| SR399 | Hexafunctional monomer ex. Sartomer | 10 | 10 |
| Genorad 16 | Stabilizer ex. Rahn | 2 | 2 |
| Ebecryl 350 | Acrylated silicone ex. Cytec | 0.04 | 0.04 |
| MPP 620XXF | Polyethylene wax ex. Kromachen | 2 | 2 |
| Total | | 100.00 | 100.00 |

TABLE 18

Flexo inks containing standard photoinitiator package (Std)

| | Yellow (Std) | Magenta (Std) | Cyan (Std) | Black (Std) |
| --- | --- | --- | --- | --- |
| Standard Technology Varnish (A) | 48 | 50 | 50 | 50 |
| Yellow pigment conc. containing 27% CI PY 126 | 50 | | | |
| Magenta pigment conc. containing 34% CI PR 57:1 | | 50 | | |
| Cyan pigment conc. containing 30% CI PB 15:4 | | | 50 | 3 |
| Black pigment conc. containing 30.3% CI PN 7 | | | | 43 |
| Violet pigment conc. containing 23% CI PV 23 | | | | 4 |
| SR455LM Trifunctional monomer ex. Sartomer | 2 | | | |
| Total | 100 | 100 | 100 | 100 |

TABLE 19

Flexo inks containing inventive photoinitiator package (Inv)

| | Yellow (Inv) | Magenta (Inv) | Cyan (Inv) | Black (Inv) |
| --- | --- | --- | --- | --- |
| Inventive Technology Varnish (B) | 48 | 50 | 50 | 50 |
| Yellow pigment conc. containing 27% CI PY 126 | 50 | | | |
| Magenta pigment conc. containing 34% CI PR 57:1 | | 50 | | |
| Cyan pigment conc. containing 30% CI PB 15:4 | | | 50 | 3 |
| Black pigment conc. containing 30.3% CI PN 7 | | | | 43 |
| Violet pigment conc. containing 23% CI PV 23 | | | | 4 |
| SR455LM Trifunctional monomer ex. Sartomer | 2 | | | |
| Total | 100 | 100 | 100 | 100 |

These inks were printed onto Avery Dennison PE85 Top-Trans Label substrate using a 400/5 anilox on an Easiproof flexo proofer. The prints were cured under a medium pressure mercury arc lamp on a laboratory UV curing rig from IST with a dose of 33 mJ per pass. The number of passes required to cure was measured by a "set-off cure test" which is done by visually comparing the extent to which, after each pass, the ink has transferred to a piece of blank carton board substrate under a pressure of 10 tons for 5 seconds. Decreased ink transfer is a measure of superior cure and hardness.

For all of the 8 inks tested, complete cure was achieved in 2 passes under the UV lamp, and in all cases, based on the amount of set-off ink transfer visually assessed after the first pass, the inks containing the photoinitiator of Inventive Example 18 (yellow-inv, magenta-inv, cyan-inv and black-inv) were at least as fast curing as their respective standard formulations (yellow-std, magenta-std, cyan-std and black-std).

These results demonstrate good utility of the inventive photoinitiators technology in UV flexo inks.

Example 30

Photoinitiator Migration

A UV flexo black ink was prepared as shown in Table 20 to show the possible use of the ketocoumarin materials of the present invention in low migration applications.

TABLE 20

| | Black-mig |
| --- | --- |
| Inventive Technology Varnish (B) as defined in Table 17 | 48.5 |
| Black pigment conc. containing 30.3% CI PN 7 | 50 |
| SR455LM Trifunctional monomer ex Sartomer | 1.5 |
| Total | 100.00 |

The black ink [black-mig] defined in Table 20 above was printed onto polyethylene coated board substrate using a 400/5 anilox on an Easiproof flexo proofer, and was cured at a dose of 158 mJ using a laboratory UV curing rig from IST fitted with a standard medium pressure mercury arc lamp. A print area totaling 100 $cm^2$ was covered with a thin grade polyethylene and sandwiched between two layers of aluminum foil before being put under a pressure of 10 tons for 48 hours in a Specac hydraulic press. The polyethylene film was then submerged in 20 ml of ethanol for 24 hours and the solution then analyzed for components migrating out of the ink by a set-off migration mechanism using LC-MS.

The photoinitiator Inventive Example 18 was found not to be detected as a migrating species, with a detection limit of 1.5 ppb (EU food model). These results demonstrate that the Inventive photoinitiator technology would be acceptable for use as a low migration photoinitiator in UV food packaging applications. Similar results could reasonably be expected using the inventive photoinitiators technology in other low migration printing applications with printing application methods such as Offset, Screen, Inkjet, Gravure and Intaglio.

What is claimed is:

1. A compound of formula (I):

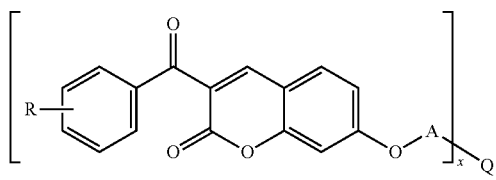

where:
R is an alkyl or alkoxy substituents;
A=—$CH_2$—$R^1$—$(CH_2)_n$—$[O(CHR^2CHR^3)_a]_y$—, where
n=0 or 1
a=1 to 2
$R^1$=—C=O or —CH(OH)—
y=0 to 10,
one of $R^2$ and $R^3$ represents a hydrogen atom and the other represents a hydrogen atom, methyl group or ethyl group;
Q is a residue selected from the group consisting of: monohydroxy compounds having from 1 to 6 hydroxy groups, polyhydroxy compounds having from 1 to 6 hydroxy groups, and $C_2$-$C_{12}$ polyalkylene glycols in which the alkylene part has from 2 to 12 carbon atoms; and
x is an integer from 1 to 6.

2. The compound of claim 1, where Q is a residue of polyhydroxy compounds selected from the group consisting of: ethylene glycol, propylene glycol, butylene glycol, glycerol, 2,2-propanediol, polyethylene glycol, polypropylene glycol, polybutylene glycol, trimethylolpropane, di-trimethylolpropane, pentaerythritol and di-pentaerythritol.

3. The compound of claim 1, where Q is a residue of monohydroxy compounds selected from the group consisting of: a compound of formula $R^4$—OH where $R^4$ is a $C_1$ to $C_{12}$ alkyl group, and a group of formula —$[O(CHR^2CHR^3)_a]_y$—$OCH_3$ where a is a number from 1-2, y is a number from 0 to 10, and $R^2$ and $R^3$ are the same or different and each represents a hydrogen atom or a $C_1$-$C_4$ alkyl group.

4. The compound of claim 1, where Q is a residue of polyalkylene glycols selected from the group consisting of: butane-1,4-diol, hexane-1,6-diol, octane-1,8-diol, decane-1,10-diol and dodecane-1,12-diol.

5. The compound according to claim 1, wherein x=1.

6. The compound of claim 1 having the structure:

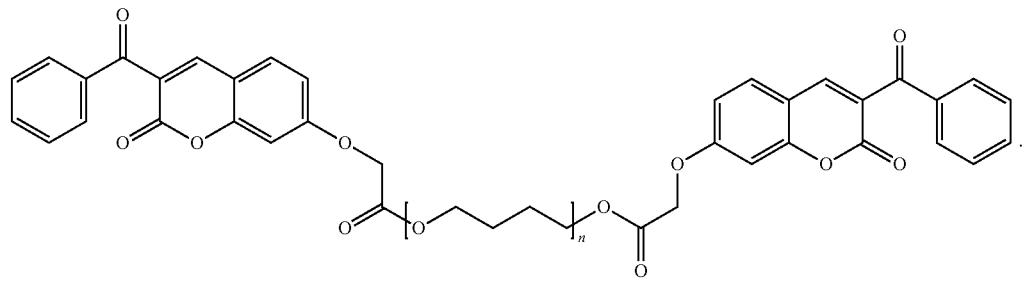

7. The compound of claim 1 having the structure:

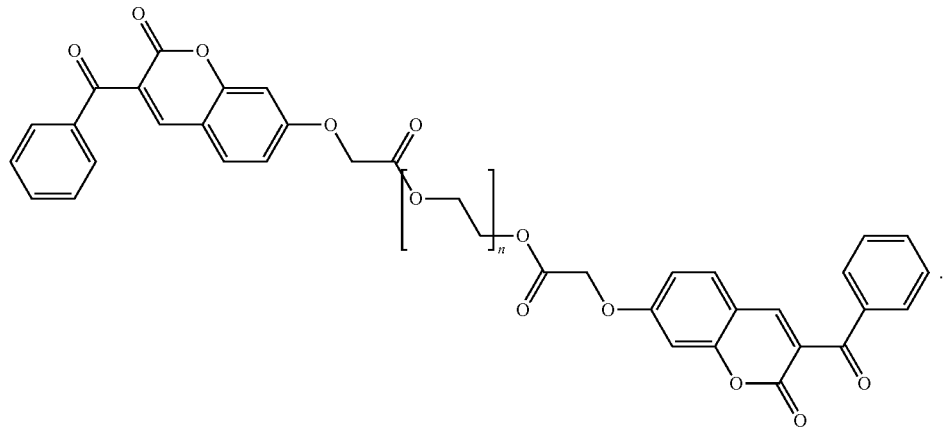

8. The compound of claim 1 having the structure:

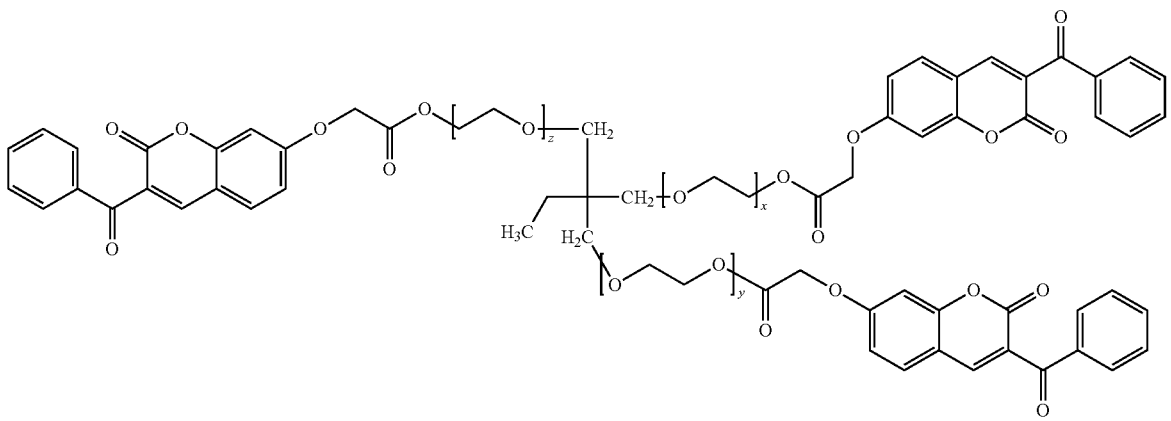

Where x+y+z=3.

9. The compound of claim 1 having the structure:

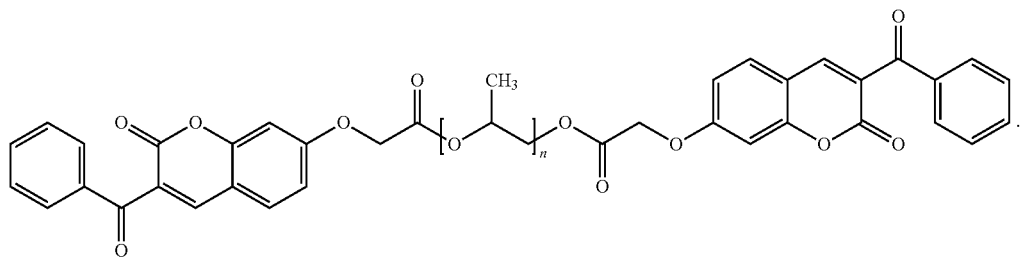

10. A radiation curable composition comprising the compound of claim 1.

11. The radiation curable composition of claim 10, wherein the composition is selected from the group consisting of radiation curable coatings, printing inks, varnishes and adhesives.

12. The radiation curable composition of claim 11 further comprising one or more materials selected from the group consisting of polymerizable monomers, prepolymers, oligomers, other photoinitiators, an amine synergist and sensitizers.

13. The radiation curable composition of claim 12 further comprising one or more materials selected from the group consisting of waxes, flow aids, stabilizers, colorants, defoamers, dispersants, silicones, rheological modifiers and plasticizers.

14. A method of preparing a cured polymeric composition comprising exposing a radiation curable coating composition containing the compound of claim 1 to actinic radiation.

15. A method according to claim 14, in which the actinic radiation is ultraviolet radiation.

16. A method of preparing a radiation curable composition comprising combining the compound of claim 1 with one or more materials selected from the group consisting of polymerizable monomers, prepolymers, oligomers, other photoinitiators, amine synergists and sensitizers.

17. The method of claim 16, wherein the radiation curable composition is selected from the group consisting of inks, coatings, varnishes and adhesives.

18. The method of claim 16, wherein the radiation curable composition is suitable for food packaging.

19. The radiation curable composition of claim 10, wherein the compound of claim 1 has the structure:

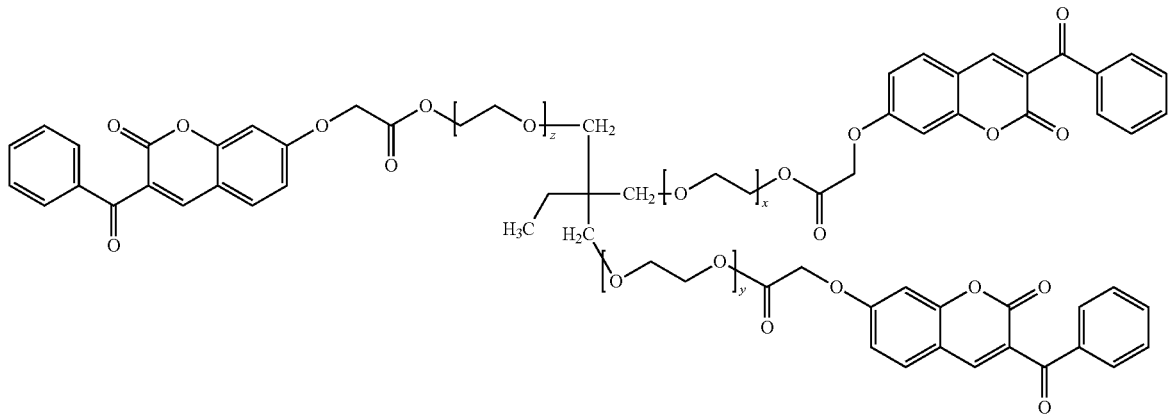

Where x+y+z=3.

20. The method of claim 16, wherein the compound of claim 1 has the structure:
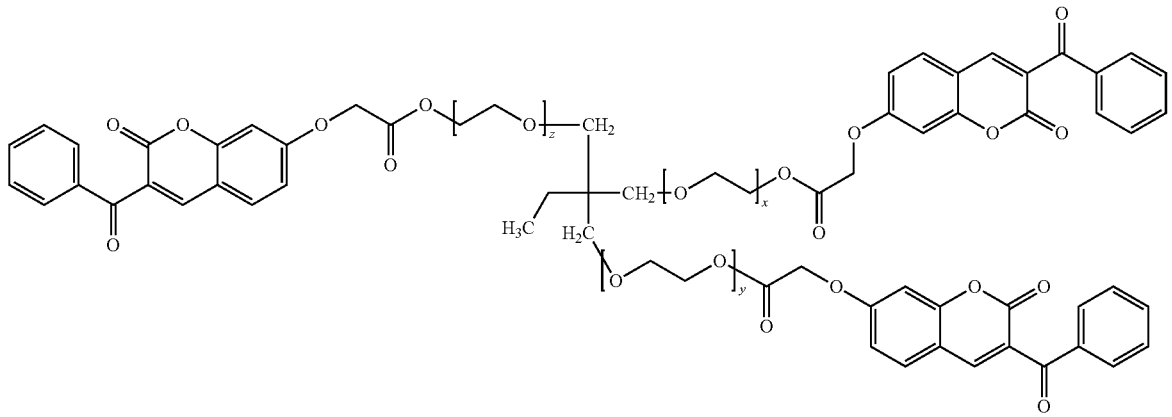
Where x+y+z=3.
* * * * *